(12) United States Patent
Rodrigues et al.

(10) Patent No.: US 9,566,363 B2
(45) Date of Patent: Feb. 14, 2017

(54) MICROBICIDAL COMPOSITE MATERIAL

(71) Applicant: SHAKTHI KNITTING LIMITED, Tirupur (IN)

(72) Inventors: Michael Rodrigues, Tirupur (IN); Siddamalai Gounder Krishnaswamy Vivekananda, Tirupur (IN); Sundaravadivelu Vasanth Kumar, Tirupur (IN)

(73) Assignee: Shakthi Knitting Limited, Tirupur (IN)

( * ) Notice: Subject to any disclaimer, the term of this patent is extended or adjusted under 35 U.S.C. 154(b) by 0 days.

(21) Appl. No.: 14/412,109

(22) PCT Filed: May 15, 2014

(86) PCT No.: PCT/IB2014/000735
§ 371 (c)(1),
(2) Date: Dec. 30, 2014

(87) PCT Pub. No.: WO2014/184640
PCT Pub. Date: Nov. 20, 2014

(65) Prior Publication Data
US 2016/0051720 A1 Feb. 25, 2016

(30) Foreign Application Priority Data

May 17, 2013 (IN) .......................... 2188/CHE/2013

(51) Int. Cl.
| | |
|---|---|
| *A61L 15/44* | (2006.01) |
| *A61L 31/14* | (2006.01) |
| *A61L 31/16* | (2006.01) |
| *A61L 15/42* | (2006.01) |
| *A01N 25/34* | (2006.01) |
| *A01N 55/00* | (2006.01) |
| *A61F 13/00* | (2006.01) |

(52) U.S. Cl.
CPC .............. *A61L 15/44* (2013.01); *A01N 25/34* (2013.01); *A01N 55/00* (2013.01); *A61F 13/00029* (2013.01); *A61L 15/425* (2013.01); *A61L 31/146* (2013.01); *A61L 31/16* (2013.01); *A61F 2013/00238* (2013.01); *A61L 2300/208* (2013.01); *A61L 2300/216* (2013.01); *A61L 2300/404* (2013.01); *A61L 2400/12* (2013.01)

(58) Field of Classification Search
CPC ...... A61L 31/146; A61L 31/16; A61L 15/425; A61L 2300/404; A61F 13/00029
USPC ................................ 424/405; 514/63; 602/44
See application file for complete search history.

(56) References Cited

U.S. PATENT DOCUMENTS

| | | | | |
|---|---|---|---|---|
| 4,394,378 A | * | 7/1983 | Klein ..................... | C07F 7/1836 504/153 |
| 2009/0130160 A1 | * | 5/2009 | Dugan ................... | A61K 33/38 424/407 |
| 2012/0315225 A1 | * | 12/2012 | Porbeni ................... | A61L 15/26 424/49 |

FOREIGN PATENT DOCUMENTS

| | | |
|---|---|---|
| GB | 2 302 669 A | 1/1997 |
| WO | WO 2009068713 A1 | 6/2009 |

OTHER PUBLICATIONS

International Search Report received in PCT Application No. PCT/IB2014/000735 dated Jul. 18, 2014.

* cited by examiner

*Primary Examiner* — Yanzhi Zhang
(74) *Attorney, Agent, or Firm* — Brinks Gilson & Lione

(57) ABSTRACT

A composite material having inherent microbicidal activity is herewith described. The microbicidal composite material comprises of a first layer having a first predefined thickness and a first predefined stitch/thread density; a second layer having a second predefined thickness and a second predefined stitch/thread density; an intermediate layer having a third predefined thickness and a third predefined stitch/thread density, wherein the intermediate layer is sandwiched between the first layer and the second layer, and where the intermediate layer is connected to the first layer and the second layer to form a three dimensional structure, and where each layer in the three dimensional structure has a plurality of apertures. Further, at least one layer in the three dimensional structure comprises at least one of microfibers and nanofibers having augmented surface moieties, wherein the augmented surface moieties allow for binding of a microbicidal agent to impart the inherent microbicidal activity.

29 Claims, 19 Drawing Sheets

US 9,566,363 B2

MICROBICIDAL COMPOSITE MATERIAL

RELATED APPLICATIONS

This application is a 371 application of PCT/IB2014/000735 having an international filing date of May 15, 2014, which claims priority to Indian application No. 2188/CHE/2013 filed May 17, 2013, the entire contents of which are incorporated herein by reference.

TECHNICAL FIELD

The present subject matter relates, in general, to a composite material and, particularly but not exclusively, to the composite material having a microbicidal activity.

BACKGROUND

The advancement in technology has led to a considerable research being conducted on the application of microbicidal agents on fibres and fabrics, that would effectively retard the growth of various microorganisms. For example, sanitary wipes used for cleaning environmental, food contact surfaces, and personal and health care applications incorporate various microbicidal agents on its fabric to exhibit sanitizing and microbicidal properties. Although several new drugs have now emerged for the treatment of drug resistant infections, the microorganisms that are treated with these new drugs are becoming increasingly drug resistant resulting in the creation of superbugs. There is emerging need to develop a mechanism to kill the microbes commonly referred as pathogens by techniques that do not cause drug resistance in them.

BRIEF DESCRIPTION OF DRAWINGS

The detailed description is described with reference to the accompanying figures. In the figures, the left-most digit of a reference number identifies the figure in which the reference number first appears. The same numbers are used throughout the drawings to reference like features and components.

DETAILED DESCRIPTION

Figure 1A:
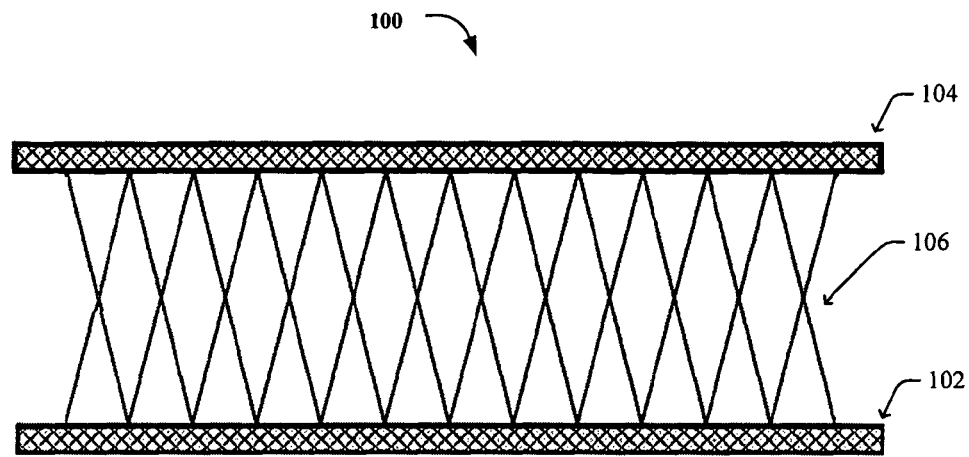
FIG. 1a illustrates cross-sectional view of a microbicidal composite material, in accordance with an embodiment of the present subject matter.

A composite material exhibiting a microbicidal activity is herewith described. Although the description herewith provided is in reference to usage of the microbicidal composite material in bandages for the purpose of wound healing, it may be understood, that the microbicidal composite material may be used in other products, such as sanitary pad, tampons, toilet accessories, diaper, sanitary wipe, surgical gown, surgical glove, surgical scrub, mattress covers, beddings, bedding sheets and pillow covers, operation theatre covers, hospital examination table covers, hospital bio waste disposable bags, hospital curtains, air conditioning filters, water filters, face mask, meat storage and packing materials, and other products as may be understood by a person skilled in the art, to exhibit microbicidal properties.

Conventional composite materials that are used for wound healing purposes have a microbicidal agent incorporated on the surface of the composite material to exhibit microbicidal activity. These composite materials allow for absorption of exudates from the surface of the wound; and the microbicidal agent incorporated on its surface enables the property of limiting pathogen growth. An example of a conventionally used microbicidal agents are silver salts, which are coated over a substrate of the composite material. However, such an application of the microbicidal agent on the surface of the composite material results in eluting of the microbicidal agent back into the wound. Such eluting of the microbicidal agent may interfere with the normal wound healing process. Further, eluting of the microbicidal agent on the wound may make the pathogens in the wound more resistant to the silver, thereby facilitating evolution of superbugs. These superbugs are significantly resistant to silver particles or normal drugs that are meant to kill the pathogens. Further the eluting of substances from the material depletes the material, reducing the performance of the material over time. Hence, such composite materials that are used in wound healing may have to be replaced frequently for faster healing of the wound.

Certain other composite materials that are conventionally used for wound healing are coated with the microbicidal agent on one of the surfaces to exhibit microbicidal activity; and the composite material is provided with limited or no porosity on the other surface, in order to prevent pathogens present in the air from entering the wound. Such a restricted supply has two major disadvantages. First it gives rise to anaerobic conditions on wound which promotes the growth of anaerobic microbes and proliferates with time and secondly it may result in an inadequate circulation of oxygen to the wounded tissues, thereby resulting in delayed healing of the wound.

Also, the conventionally used composite materials are structured in such a manner that allow for limited absorption of exudates from the surface of the wound. Such a limitation may necessitate the need for frequent replacement of the composite material for faster wound healing. However, changing the microbicidal composite material at frequent intervals may cause of great discomfort to the user physically. Any significant delay in replacing the composite material laden with exudates is seen to have negative effect on wound healing by facilitating proliferation of pathogens in the exudates of the wound and increasing the toxic load on wound which may be a dangerous mix of body toxins causing inflammation and swelling, thereby exposing the person to a greater risk for severe wound infections.

A three dimensional structure of a microbicidal composite material is herein described, in accordance with an implementation of the present subject matter. The described structure allows for efficient air circulation, thereby facilitating increased supply of oxygen to the wounded issues, and simultaneously restricts the entry of pathogens from the air entering into the wound, thereby alleviating the wound healing process. The described structure also allows for efficient wicking of the exudates from the surface of the wound by capillary action, thereby preventing the exudates on the wound to serve as a nutrient medium for multiplication of the pathogens. The described structure is also provided with increased number of surface moieties along layers of the composite material, thereby allowing for stronger and quantitatively larger binding of the microbicidal agent with the composite material. The surface moieties include functional groups that are available for the chemical bonding of the microbicidal agent. In an example, the chemical binding of the microbicidal agent to the surface moieties is via a covalent bonding. Such an interaction prevents eluting of the microbicidal agent into the wound thereby preventing the evolution of drug resistant microbes.

According to an implementation of the present subject matter, the microbicidal composite material comprises of a first layer, an intermediate layer, and a second layer, where each of the layers are aligned such that, the intermediate layer is sandwiched between the first layer and the second layer, and where the intermediate layer is connected, with the first layer and the second layer, to form a three dimensional structure. As known to practitioners of the art the interlayer connection can be made using the method of spacer knitting. Further each layer in the three dimensional structure has multiplicity of apertures, where each of the one or more apertures are of a predefined size. In an example, the predefined size of each of the one or more apertures in the three dimensional structure having the predefined size is controlled to allow for selective permeation of gases and fluids from the wound, thorough the three dimensional structure. Further, such a microbicidal composite material, having one or more apertures, when used in part or as a whole in, allows for efficient circulation of oxygen to the wounded tissues, thereby alleviating the wound healing process. The three dimensional structure which has the microbicidal spears all along the surfaces of the composite, kills the pathogens that are present in the air while passing through the composite. It kills the airborne pathogens when the air is entering the dressing material before reaching the wound tissue. The bonding can also be made by use of primers in case of fibres where free hydroxyl groups are not available for the formation of covalent bond.

Further, each layer of the microbicidal composite material, i.e., the first layer, the second layer, and the intermediate layer are associated with a first pre-defined stitch/thread density, second pre-defined stitch/thread density, and a third pre-defined stitch/thread density, respectively. In an implementation, the third pre-defined stitch/thread density is lesser than that of the first pre-defined stitch/thread density and the second pre-defined stitch/thread density. Such a differential stitch/thread density allows for wicking by capillary action on contact of at least one of the first layer and the second layer with a fluid. The use of such a microbicidal composite material either in whole or in part of a wound dressing may be particularly helpful to promote healing of a wound, where the differential stitch/thread density allows for wicking exudates away from the wound, through one of the first layer and second layer on contact with the wound. This enhanced wicking feature ensures that, the exudates in the vicinity of the wound is effectively removed ensuring that it may no longer serve as a nutrient medium for the growth of pathogens, thereby facilitating wound healing. The exudate which is now held away from the wound is allowed to dry slowly by simple evaporation method promoted by the air circulation through the permeable microbicidal composite material. Also the pathogens present in the exudate are killed by the composite material thus ensuring that the spread of infections is curtailed. The wicking happens in such a way that the wound is left sufficiently moist for enabling the body to ensure healing without interfering in normal body healing mechanism.

Furthermore, at least one layer in the microbicidal composite material is composed of microfibers or nanofibers, thereby increasing the available surface area for binding on the microbicidal agent to the microbicidal composite material. Such an augmented surface area results in augmented moieties may allow for greater concentration of a microbicidal agent binding to the augmented surface moieties. The composite thus becomes an intrinsically microbicidal composite material. In an implementation, the use of the microbicidal composite material either as whole or in part of a wound dressing may prevent eluting of the microbicidal agent into the wound thereby promoting faster healing of the wound and also prevents the evolution of drug resistant microbes.

The described structure allows for efficient air circulation, thereby facilitating increased supply of oxygen to the wounded tissues, and simultaneously restricts the entry of pathogens from the air entering into the wound, thereby alleviating the wound healing process. The described structure also allows for efficient wicking of the exudates from the surface of the wound by capillary action, thereby preventing the exudates on the wound to serve as a nutrient medium for multiplication of the pathogens. The described structure also provides for increased number of surface moieties in layers of the composite material, thereby allowing for stronger and larger amount of the microbicidal agent binding with the composite material. Such an interaction may prevent eluting of the microbicidal agent from the vicinity of the wound and thus provide for a continued larger concentration of the microbicidal agent, keeping a higher kill rate of pathogens on the wound, from the exudates and from the air coming in contact with the wound without interfering in normal wound healing, thereby promoting faster healing of the wound and also preventing the evolution of drug resistant microbes.

The following detailed description includes references to the accompanying drawings, which form part of the detailed description. The drawings show illustrations in accordance with example embodiments. These example embodiments are described in enough detail to enable those skilled in the art to practice the present subject matter. However, it will be apparent to one of ordinary skill in the art that the present subject matter may be practiced without these specific details. The embodiments can be combined, other embodiments can be utilized or structural and logical changes can be made without departing from the scope of the subject matter. The following detailed description is, therefore, not to be taken as a limiting sense.

In this document, the terms "a" or "an" are used, as is common in patent documents, to include one or more than one. In this document, the term "or" is used to refer to a nonexclusive "or," such that "A or B" includes "A but not B," "B but not A," and "A and B," unless otherwise indicated.

FIG. 1a illustrates a cross sectional view of a microbicidal composite material 100 for wicking of fluids, in accordance with an embodiment of the present subject matter. The microbicidal composite material of the present subject matter may be used as a whole or a part in one or more of a sanitary pad, tampons, toilet accessories, diaper, sanitary wipe, surgical gown, surgical glove, surgical scrub, mattress covers, beddings, bedding sheets and pillow covers, operation theatre covers, hospital examination table covers, hospital bio waste disposable bags, hospital curtains, air conditioning filters, water filters, face mask, meat storage and packing materials, and other products as may be understood by a person skilled in the art, to exhibit microbicidal properties.

The microbicidal composite material 100 comprises a first layer 102, a second layer 104, and an intermediate layer 106, where the intermediate layer 106 is sandwiched between the first layer 102 and the second layer 104, and where the intermediate layer 106 is connected to the first layer 102 and the second layer 104 to form a three dimensional structure. In an implementation, the three dimensional structure may be formed with a single material or with a combination of materials to form a knitted structure, woven structure or a non-woven structure.

In an embodiment, the one or more material may be made by fibres, filaments, yarns and fabrics or combinations thereof. Examples of the material can include, but not limited to synthetic fibres, natural fibres, or combinations thereof. Synthetic fibres include, for example, acrylic, polyamide, polyolefin, polyaramide, polyurethane, poly acylonitriles, textured polyethylene terephthalate, polytriphenylene terephthalate, polybutylene terephthalate, polylactic acid, aramides, metaramides and combinations thereof. Polyamide includes, for example, nylon 6, nylon 6.6, and combinations thereof. In an example, the polyolefin's includes, for example, polypropylene, polyethylene; and combinations thereof. Polyaramide includes, for example, poly-p-phenyleneteraphthalamide, poly-m-phenyleneteraphthalamid, and combinations thereof. Natural fibres include, for example, wool, cotton, flax, rayon, jute, linen and blends thereof.

In an implementation, at least one layer in the three dimensional structure is composed of an elastomeric material, and wherein the elastomeric material includes at least one of a textured yarns, textured fibres, multi component yarns, multi component fibres, polyurethane and natural rubber to impart resilient property. In another implementation, a breathable film is applied to any one of the layer to cover it fully such that it is permeable for the gaseous exchange like vapour from the wound and air from atmosphere to the wound but limiting external water or chemicals soling the wound. In an example, at least one layer of the three dimensional structure may be composed of biopolymers, where the biopolymers include at least one selected from a group of poly lactic acid, poly glycolic acid and caprolactam. These biopolymers have a defined biodegradable and bio disintegration action, where the polymer gets broken to monomeric entities, which are absorbed and eliminated in the normal body functions. The biopolymers can be engineered for sustained or time dependent disintegration. These bioactive agents can be embedded with biopolymers to impart sustained and time dependent release of the bioactive agents. The bioactive agents include at least one selected from the group of vitamins, minerals, anti inflammatory agents, antibiotics, antiseptic, haemostatic agents and analgesics. The application of these bioactive agents at least on one layer of the composite allows faster wound healing and delivery of nutrients. The variants of bioactive agents can be used depending on the type of wound.

Further, each layer in the three dimensional structure is composed of one or more apertures, where each of the one or more apertures is associated with a pre-determined size. As known to practitioners of the art of weaving, knitting and spacer knitting, the pre-determined size of the apertures may be controlled by the course per inch and wales per inch of the weaving, knitting and spacer knitting processes. This pre-determined size of the one or more apertures in each of the one or more layers of the three dimensional structure is controlled to allow for selective permeation of fluids and gases. The one or more apertures in the three dimensional structure imparts the characteristics breathability to the microbicidal composite material 100.

In an implementation, the pre-determined size may be controlled by adjusting stitch/thread density of the material in each layer of the three dimensional structure. For example, each layer of the microbicidal composite material 100, i.e., the first layer 102, the second layer 104, and the intermediate layer 106 are associated with a first pre-defined stitch/thread density, second pre-defined stitch/thread density, and a third pre-defined stitch/thread density. As known to practitioners in this art the stitch/thread density of these layers can be controlled by in the process of weaving, process of knitting, spacer knitting and non-woven process. In an example, where the technique of manufacture is one of knitting, spacer knitting and weaving, first pre-defined stitch/thread density may be in the range of 20 Course per Inch to 60 Course per Inch, and 20 Wales per Inch to 60 Wales per Inch. The second pre-defined stitch/thread density may be the range of 20 Course per Inch to 60 Course per Inch, and 20 Wales per Inch to 60 Wales per Inch. As known to practitioners in this art the stitch/thread density of these layers can be controlled by in the process of weaving, process of knitting, process of spacer knitting and non-woven process the third pre-defined stitch/thread density may be in the range of 20 Piles Course per Inch to 70 Piles Course per Inch, and 30 Piles Wales per Inch to 50 Piles Wales per Inch. In an implementation, the third pre-defined stitch/thread density is lesser than that of the first pre-defined stitch/thread density and the second pre-defined stitch/thread density. Such a differential stitch/thread density allows for wicking by capillary action on contact of at least one of the first layer 102 and the second layer 104 with a fluid.

Furthermore, each layer of the microbicidal composite material 100, i.e., the first layer 102, the second layer 104, and the intermediate layer 106 are associated with a first pre-defined thickness, second pre-defined thickness and a third pre-defined thickness. In an implementation, at least one layer has a pre-defined thickness greater than an adjacent layer in the three dimensional structure. For instance, the third pre-defined thickness may be greater than the first pre-defined thickness and the second pre-defined thickness. In an example, the first pre-defined thickness is in the range of 100 micron to 1000 micron. The second pre-defined thickness is in the range of 100 micron to 1000 micron; and the third pre-defined thickness is in the range of 600 micron to 6000 micron. Such an increased thickness in the intermediate layer 106 may result in a stitch/thread density gradient in the layers to enhance the wicking action. In an example in this subject matter the composite material 100 was spacer knitted using a mixture of 90% textured polyethylene terephthalate and 10% of polyurethane, with a thickness 200 microns for the first layer, a thickness 200 microns for the second layer and a thickness 700 microns for the third layer. In the example, the spacer knitting process used 46 Course per inch and 42 Wales per inch for the first layer and the second layers and 20 Course per inch and 20 Wales per inch for the third layer.

Further, the augmentation of surface moieties as explained may allow for greater concentration of a microbicidal agent binding to the augmented surface moieties. In an example, the microbicidal agent is represented by general formula-I.

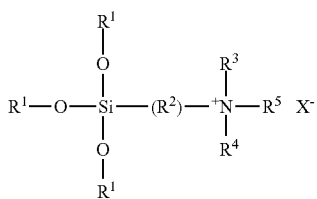

Formula-I wherein:
$R^1$=hydrogen and/or $C_1$ to $C_4$ alkyl;
$R^2$=divalent hydrocarbon radical with $C_1$ to $C_8$ carbon atoms;
$R^3$=hydrogen or $C_1$ to $C_4$ alkyl;
$R^4$=hydrogen or $C_1$ to $C_{10}$ alkyl;
$R^5$=$C_8$ to $C_{22}$ saturated or unsaturated hydrocarbon radical; and
X=alkyl halide.

In an implementation, the microbicidal agent is one of a 3-(trimethoxysilyl)propyl-N-octadecyl-N,N-dimethyl ammonium chloride, 3-(trimethoxysilyl)propyl-N-tetradecyl-N,N-dimethyl ammonium chloride, 3-(trimethoxysilyl) propyl-N,N-didecyl-N-methyl ammonium chloride, 3-(trihydroxysilyl) propyl-N-octadecyl-N,N-dimethyl ammonium chloride. In an example, the microbicidal agent is preferably 3-(trimethoxysilyl) propyl-N-tetradecyl-N,N-dimethyl ammonium chloride.

The steps employed for binding of the microbicidal agent to the microbicidal composite material 100 structure are herewith described. The composite material 100 is treated with the microbicidal compound as represented by formula 1 by padding it in a solution of the said microbicidal compound wherein the microbicidal compound is the solute and the solvent is chosen appropriately depending on the solubility characteristics of the microbicidal compound. The chosen solvent can be one of or a mixture of a de-mineralized/sterilized water, a suitable alcohol, such as, ethanol, methanol, isopropanol, methyl triglycol pH buffered acetic acid/sodium acetate and an organic acid like formic, citric or acetic acid. The solution concentration is generally in the range of 0.05% to 2.5% on weight of the microbicidal composite material 100. This may further depend on the type of polymer constituting the dimensional structure and the thickness and type of the dimensional structure in terms of its surface moieties available for reaction. In an example in this subject matter a mixture of methyl triglycol ($CH_3$($OCH_2CH_2$)$_3$—OH) along with water was used as solvent suitable to the microbicidal compound 3-(trimethoxysilyl) propyl-N-tetradecyl-N, N-dimethyl ammonium chloride used as the microbicidal agent. In the example, the concentration of the microbicidal compound in the padding bath was held at a concentration of 1.00% on weight of the microbicidal composite material 100.

As known to practitioners of this art the solution is taken in treatment bath of the padding machine like a stenter and the composite material is passed through the bath of the microbicidal compound at a predetermined speed. The speed is optimized such that the amount of residence time in the bath is in the range of 3 to 10 seconds, for the chemical compound to transfer from the bath to the composite material. The concentration of the microbicidal compound in the padding bath is held in the range of 0.05% to 5% w/w on weight of the microbicidal composite material 100 right through the process. This process ensures that the coating is uniform in the layers that constitute the composite material 100.

The amount of residence of the composite material 100 in the bath is adjusted depending on the density and thickness of the three layers of the composite material 100. In the example it was held at 3 seconds. The three dimensional structure is further squeezed to remove the excess amount of microbicidal agent from the three dimensional structure by means of padding rollers forming a padding nip. After this treatment the coated composite material passes through a drying process with drying temperature held between 100 Deg C. to 160 Degree C. depending on the solvent used in the process.

The final step is a curing step that promotes cross linking to form a polymer. This curing temperature is in the range 150 Deg C. to 200 Deg C. 8 depending on the drying temperature of the previous step ensuring that the curing temp is higher than the drying temperature by 30 Deg C. to 40 Deg C. With this cross linking the microbicidal component now becomes an integral part of the composite material 100. In this curing stage the formation of the Si—O—Si condensation moiety, links the individually distributed microbicidal compound moieties to each other. Some of the moieties have their —Si—O bond to the fabric material and thus the cross linked compound polymer is held bound to the composite material 100. In the example the link of the —Si—O is to the fabric of knitted composite material 100. In another embodiment the application of the microbicidal solution described can be sprayed uniformly on both the sides of the composite material 100 and then the drying and curing process carried out.

The microbicidal composite material 100 herewith described may be used to treat a wound caused by one or more of a gram positive bacteria, gram negative bacteria, virus, and fungi. The gram positive bacteria include Methicillin-resistant *Staphylococcus Aureus* (MRSA). The microbicidal composite material 100 may also be used as a filter for sterilizing for at least one of fluid of air, water, and milk.

The described aspects may be used as a whole or in part in several products, as understood by a person skilled in the art. The use if the described medical product as a whole or part of a wound dressing to promote wound healing is here with described in FIG. 1b, in accordance with an embodiment of the present subject matter. Wound dressing materials for purposes of this application means materials which are suitable for direct exposure to wounds of any kind including but not limited to wounds, such as, burns, pressure sores, punctures, ulcers, abrasions, cuts, incisions, sores including bed sores and suture treated areas on skin.

Figure 1B:
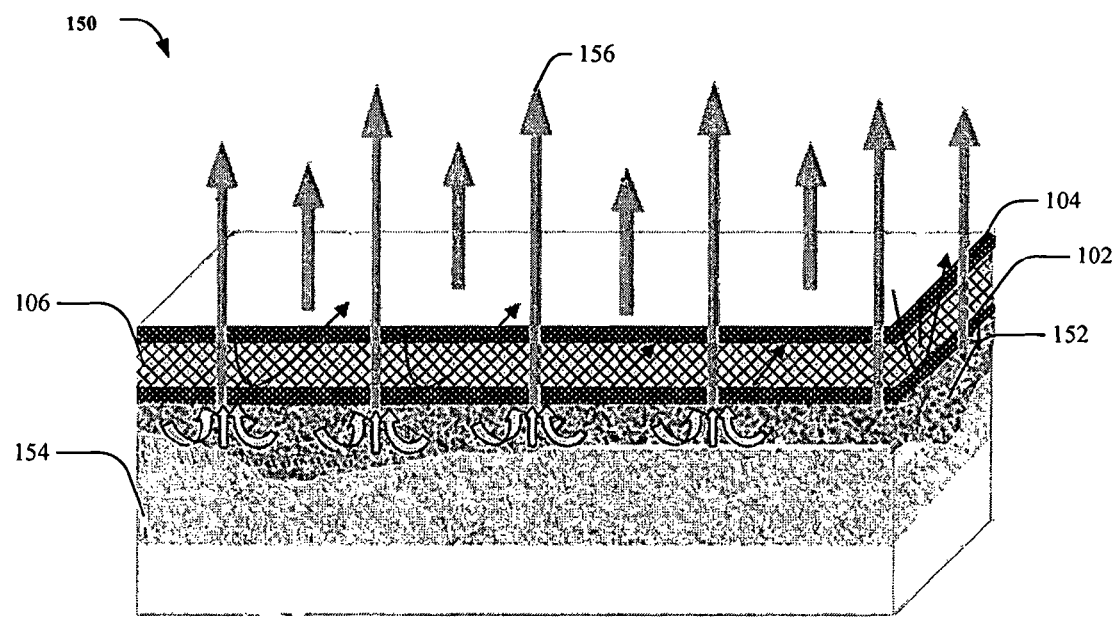
FIG. 1b is an illustration of the microbicidal composite material applied over skin on a wound, in accordance with an embodiment of the present subject matter.

In an implementation, as described in FIG. 1b the microbicidal composite material 100 is applied over the skin 154 such that the first layer 102 of the microbicidal composite material 100 is placed over the wound 152; and the second layer 104 is pervious to the atmosphere. The wound 152 may contain exudates that serve as nutrient medium for several microorganisms. Therefore, exudates management may be particularly helpful for wound healing process.

Upon placing the microbicidal composite material 100 on the wound, the exudates is wicked away from the wound 152 surface through the one or more apertures present in the first layer 102 to the subsequent layers of the microbicidal composite material 100. Such a wicking effect, by capillary action, is exerted due to the differential stitch/thread density among each subsequent layers of the microbicidal composite material 100. Such a process where the moisture of the wound are wicked from the first layer 102, and are transmitted to the subsequent layers of the microbicidal composite material 100, creates a sterile environment on the wound 152, thereby preventing the growth of microorganisms. The exudate is allowed to be vaporised and dried in the ambient conditions by simple evaporation.

Further, each layer of the microbicidal composite material 100 is pervious to gases due to the presence of one or more apertures in each layer of the microbicidal composite material 100. Therefore, the air from the second layer 104 passes through the intermediate layer 106 and the first layer 102, to the wounded tissues. This allows for effective air circulation of oxygen to the wounded tissues, thereby enabling healing of the wound 152. Besides, the pre-determined size of each aperture in the microbicidal composite material 100 is so controlled that allows for passage of vapours 156 from the wound to the atmosphere 150.

Further, the microbicidal agent incorporated in each layer of the microbicidal composite material 100 may rupture the cell membrane of the microorganisms present in the exudates, thereby controlling its growth by preventing multiplication of the microorganisms. In an example, the microbicidal agent incorporated in the microbicidal composite material 100 is bonded to the microbicidal composite material in a non-eluting manner. Non-eluting means that the agents responsible for the particular effect, such as microbicidal, are immobilized within the wound dressing, and are not eluted or eluted when exposed to aqueous fluids, menses, bodily fluids, saliva, blood, urine or wound exudates. Such non-eluting feature of the microbicidal agent in this subject matter promotes faster healing of the wound and also prevents the evolution of drug resistant microbes. In addition, the microbicidal agent incorporated in the microbicidal composite material 100 may also impart a microbicidal effect on any pathogen entering the wounded tissues during the circulation of oxygen from the external environment, thereby promoting faster healing of wounds.

Figure 2:
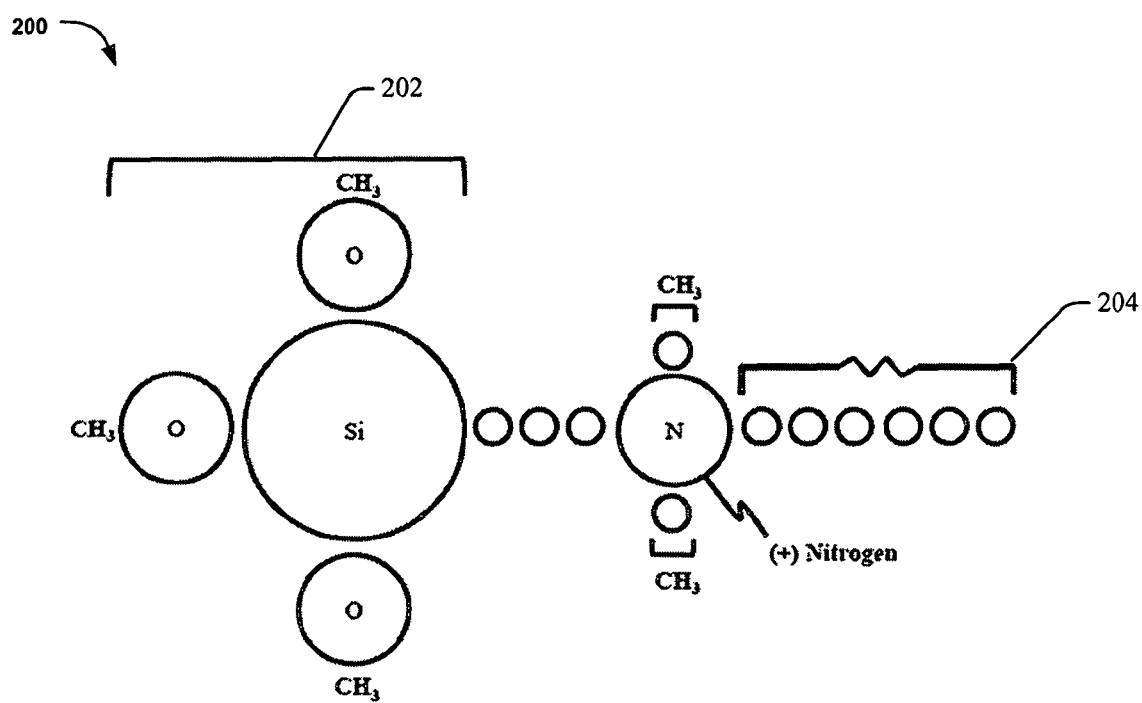
FIG. 2 is an exemplary illustration of a microbicidal agent that is an integral part of the microbicidal composite material, in accordance with an embodiment of the present subject matter.

FIG. 2 is an exemplary illustration of microbicidal agent. In the FIG. 200, it is seen as the Silicon atom bonded to three other hydrolysable groups. These hydrolysable groups, when hydrolyzed convert the organo functional group to silanols; and the silanols formed chemical bonds with each other (homopolymerization) and the microbicidal composite material 100. After the molecule has homopolymerised, it becomes an integral and permanent part of the microbicidal composite material 100. In an example, the microbicidal agent is covalently bonded to functional group of fibre to impart a non-eluting property. This dual process of the homopolymerised silanols binding to the composite material and the strong covalent coupling of the organosilane group ensures a strong binding that may be particularly helpful in promoting the wound healing process by preventing the eluting of the microbicidal agent and also prevent the evolution of superbugs. Further, it includes positively charged nitrogen and a long molecular chain 204, that are required to impart the microbicidal activity.

Figure 3A:
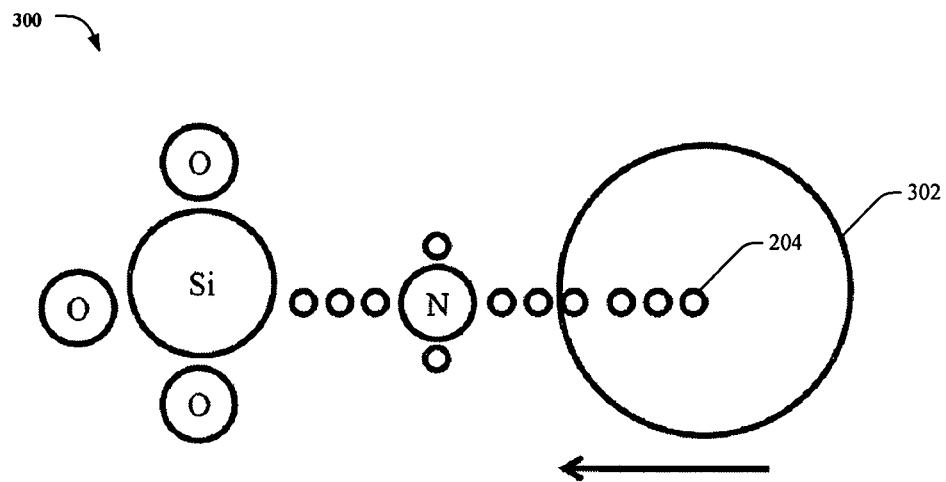
FIG. 3a illustrates a pathogen being drawn towards a positively charged nitrogen, in accordance with an embodiment of the present subject matter.

FIG. 3a illustrates a pathogen being drawn towards the positively charged nitrogen base, in accordance with an embodiment. The microbicidal agent includes a positively charged nitrogen atom. This charge along with the structure of the long molecular chain 204 acts like sword that pierces the cell membrane of all pathogens that come in contact with it, thereby killing the pathogens. As known to practitioners of the art that cell membrane damage imparts bactericidal characteristics to the microbicidal compound represented by formula-1. The effect of the charge acts in tandem to the cell membrane potential of both gram positive and gram negative pathogenic microbes thus effectively changing the cell membrane potential causing a membrane rupture. This leads to electrolyte imbalance of the pathogenic fluids causing death of pathogens.

Figure 3B:
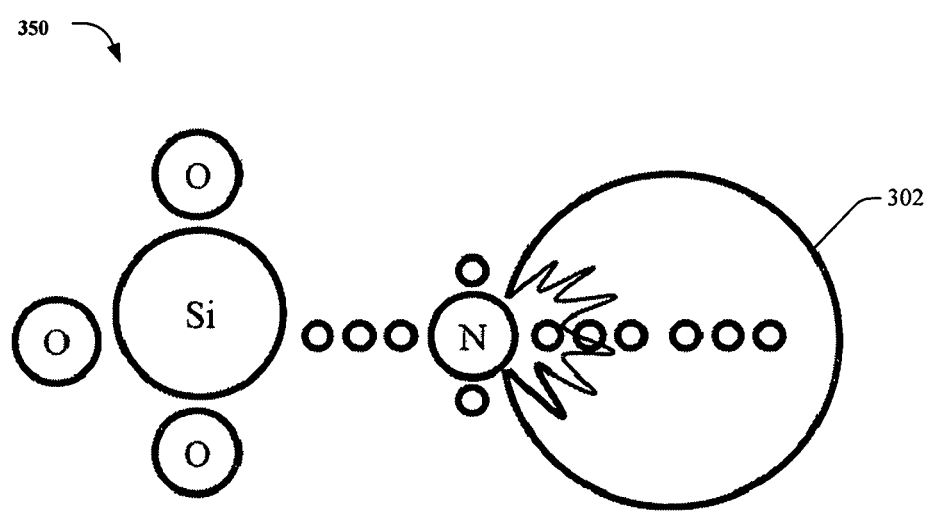
FIG. 3b illustrates rupturing a cell membrane of the pathogen, in accordance with an embodiment of the present subject matter.

FIG. 3b illustrates rupturing the cell membrane pathogen, in accordance with an embodiment. It may be noted that the aforementioned rupturing of the cell membrane of the pathogen is a physical process based on charge and length of aliphatic chain and not a chemical process. Hence, microbicidal agent is not consumed in the reaction, as a result of which the microbicidal agent is not depleted and continues to control microbial growth. Such phenomenon may be particularly helpful in wound healing, where the microbicidal composite material 100 may be used for a relatively longer period of time, before it is replaced.

The microbicidal agent according to the present subject matter has a high microbicidal activity against various microorganisms, particularly *Streptococcus, Enterococcus, Staphylococcus, Escherichia, Salmonella, Yersinia, Vibrio, Pseudomonas, Bacillus, Candida*, and so on; more specifically, *Streptococcus pneumoniae, Streptococcus pyogenes, Enterococcus faecalis, Staphylococcus aureus, Escherichia coli, Salmonella sp., Yersinia enterocolitica, Vibrio parahaemolyticus, Pseudomonas aeruginosa, Bacillus cereus, Bacillus subtilis*, and *Candida sp.* The following tests were performed in order to determine the microbicidal activity against various pathogenic organisms.

Example 1

Determination of Microbicidal Activity BS EN ISO 20645:2004

The microorganisms used in all assays were *Staphylococcus aureus* (ATCC 3658) and *Klebsiella pneumoniae* (ATCC 4352), selected according to the standards. The qualitative determination of microbicidal activity was made based on the protocol of the ISO 20645:2004. In the ISO 20645:2004 method, the textile samples were placed between two agar layers. The lower layer contained 100.1 ml of nutrient agar and the upper layer had 5±0.1 ml of nutrient agar with $2.0 \times 10^8$ cfu/ml of *Klebsiella pneumoniae*; and $3.5 \times 10^8$ cfu/ml of *Staphylococcus aureus*. The bacteria came from a previous NB inoculums incubated for 24 h at 37±2° C. The table below (table 1) illustrates the results of microbicidal effects of the microbicidal composite material 100 against *Klebsiella pneumonia* (ATCC 4352) & *Staphylococcus aureus* (ATCC 3658).

TABLE 1

| Sample Particular | Bacterial reduction in mm | Bacterial reduction in mm | Growth under fabric |
|---|---|---|---|
| Test Item | K. pneumonia ATCC 4352 1 | S. aureus ATCC 3658 4 | Absent |

Amount of sample taken: 2.5±0.5 cm circular swatches for each bacterium from the tabulation, it may be inferred that there was a significant reduction in the bacterial colony size upon exposing the sample particular. Hence, it may be understood that the microbicidal composite material shows good microbicidal effects against *Klebsiella pneumonia* (ATCC 4352) & *Staphylococcus aureus* (ATCC 3658).

Example 2

Effectiveness of Microbicidal Preservatives after Pre-Defined Time Intervals Further, the effectiveness of the microbicidal composite material 100 in wound healing is tested in accordance with the United States Pharmacopeia Microbicidal effectiveness Test (USP 51). This study is done to check the ability of the microbicidal agent, i.e., 1-Tetradecanaminium, N, N-dimethyl-N-[3-(trimethoxysilyl)propyl] used in the microbicidal composite material 100 to kill or prevent the growth of pathogens at least for seven days. Microbicidal study was carried out in five different pathogens which is shown in the Table-2 below:

TABLE 2

| | Microbicidal effectiveness test | | | |
|---|---|---|---|---|
| Test organism | Inoculums conc. (CFU's/ml) results Day 1 | Percentage of microorganism killed Day 7 | Percentage of microorganism killed Day 14 | Percentage of microorganism killed Day 28 |
| P. aeruginosa | $2.00 * 10^7$ | 100.00% | 100.00% | 100.00% |
| E. coli | $3.00 * 10^7$ | 100.00% | 100.00% | 100.00% |
| S. aureus | $11.00 * 10^6$ | 100.00% | 100.00% | 100.00% |
| Candida albicans | $2.00 * 10^6$ | 100.00% | 100.00% | 100.00% |
| Aspergillus niger | $1.00 * 10^6$ | 99.99% | 99.99% | 99.00% |

In the above table, column 1 refers to different microorganism and column 2 refers to the concentration of the inoculums taken for the study. After incubating the inoculated test product for seven days, it was observed that all the test microorganisms were killed as mentioned in the above table. In other words, the above table can be interpreted to mean that a wound can be theoretically left unattended with dressing done using the microbicidal composite material 100 for 28 days, depending on the wound type, without risk of infections. This provides comfort for the patients to do away with daily dressing changes.

Example 3

Determining the Percentage Kill Rate of Microorganisms as Per Standard ASTM 6329-98

The ASTM 6329-98 test was performed in accordance with Standard Guide for Developing Methodology for Evaluating the Ability of Indoor Materials to Support Microbial Growth Using Static Environmental Chambers. The test strains used are *Staphylococcus Aureus* ATCC 12600 (*S. aureus* ATCC 12600), *Escherichia Coli* NCIM 2065 (*E. Coli* NCIM 2065), Methicillin Resistant *Staphylococcus Aureus* (MRSA—ATCC 43300). The results are evaluated are at regular intervals and are tabulated as under Table-3 and Table-4.

TABLE 3

| | Inoculums | Bacterial kill rate (%) at a specified duration | | | |
|---|---|---|---|---|---|
| Test Strains | Strength | 30 sec | 1 min | 10 min | 30 min |
| S. aureus ATCC 12600 | $1.06 * 10^6$ Cfu/0.5 ml | — | 99.47% | 99.97% | 99.99% |
| E. Coli NCIM 2065 | $1.06 * 10^6$ Cfu/0.5 ml | — | 99.48% | 99.98% | 99.99% |
| MRSA ATCC 43300 | $1.02 * 10^6$ Cfu/0.5 ml | 99.25% | 99.52% | 99.98% | 99.98% |

TABLE 4

| | Inoculums | Bacterial kill rate (%) at a specified duration | | | |
|---|---|---|---|---|---|
| Test Strains | Strength | 1 Hrs | 4 Hrs | 8 Hrs | 12 Hrs |
| S. aureus ATCC 12600 | $1.06 * 10^6$ Cfu/0.5 ml | 99.99% | 99.99% | 99.99% | 99.99% |
| E. Coli NCIM 2065 | $1.06 * 10^6$ Cfu/0.5 ml | 99.99% | 99.99% | 99.99% | 99.99% |
| MRSA ATCC 43300 | $1.02 * 10^6$ Cfu/0.5 ml | 99.99% | 99.99% | 99.99% | 99.99% |

Example 4

Zone of Inhibition Studies with the Microbicidal Composite Material

The microbicidal composite material was tested in triplicates against *E. coli* (ATCC25922), *S. aureus* (ATCC 25923), *P. aeruginosa* (ATCC 9027) and *C. albicans* (ATCC 90028). The test material was cut as a 12 mm diameter disc and placed on 90 mm agar plates spread with 100 µl of approximately $10^8$ CFU/ml of each bacterial strain and incubated at 37±1° C. for 24 hours. For a negative control, a filter paper disc containing no antibiotic was used. The zone of inhibition (Radius in mm) around the discs was measured using a transparent ruler. The results of this test are tabulated as under Table-5.

TABLE 5

| | | ZOI (in mm) | |
|---|---|---|---|
| Organism | Name of the Test item | Mean | SD |
| Control | — | 0.00 | 0.00 |
| E. coli | The microbicidal composite material | 0.00 | 0.00 |
| | Ciprofloxacin- 1 µg/Disc | 11.00 | 1.00 |
| P. aeruginosa | The microbicidal composite material | 4.57 | 0.40 |
| | Ciprofloxacin | 9.50 | 0.50 |
| S. aureus | The microbicidal composite material | 0.00 | 0.00 |
| | Ciprofloxacin | 11.55 | 0.95 |
| C. albicans | The microbicidal composite material | 2.77 | 0.75 |
| | Flucanazole-25 µg/Disc | 3.60 | 0.40 |

After 24 hours, the discs were transferred to Nutrient broth which was then incubated at 37±1° C. for another 24 hours. The broth contents were placed on Nutrient agar plates to measure the residual percentage of microbes present on the disc as a result of remaining on a lawn of bacteria overnight. Percentage survival was calculated as [number of CFU/ml in test substance/number of CFU/ml in control substance]. The killing percentage was calculated as 100-residual percentage. The results are tabulates as under Table-6.

TABLE 6

| | The Microbicidal test | | Ciprofloxacin | |
|---|---|---|---|---|
| | Residual % | Killing % | Residual % | Killing % |
| E. coli | 0.002 | 99.9983 | 0.000 | 99.9997 |
| S. aureus | 0.009 | 99.9914 | 0.008 | 99.9921 |
| P. aeruginosa | 0.001 | 99.9992 | 0.001 | 99.9994 |
| C. albicans | 0.006 | 99.9937 | 0.010 | 99.9902 |

The results concluded that the test item, i.e., the microbicidal composite material) exhibited a significant Zone of Inhibition (ZOI) for *P. aeruginosa* and *C. albicans*, but did not exhibit significant ZOI for *E. coli* and *S. aureus*. Further, the rest item exhibited growth inhibition of test organisms in continuation of transfer of discs of ZOI assay into broth for 24 hours. The effect was comparable to that observed with a standard reference drug ciprofloxacin.

Example 5

Effect of the Microbicidal Composite Material on Bio Film Prevention and Disruption 15 millimeters (mm) Discs of the microbicidal composite material were cut and placed into 24 well plates containing approximately $10^8$ CFU/ml in Tryptic Soy Broth (TSB) of *P. aeruginosa* and *S. aureus* respectively and incubated at 37±1° C. for the Bio film Prevention assay. Similarly, 15 millimeter (mm) Discs of the microbicidal composite material were cut and placed into 24 well plates containing overnight grown culture of *P. aeruginosa* and *S. aureus* respectively in TSB and further incubated for 24 hours at 37±1° C. for the disruption assay.

Further, plain filter paper discs were placed in culture control (C) wells with approximately $10^8$ CFU/ml of the above bacteria in Tryptic Soy Broth (TSB) for both the Prevention and Disruption assay. After incubation, the contents were removed and washed four times with Phosphate Buffer saline (pH 7.2). A 500 μl of 0.1% crystal violet stain was added to each well and incubated for 20 minutes at room temperature, washed, and dried. Subsequently, 500 μl of ethanol supplemented with 2% acetic acid was added to each well for 30 min. The Optical Density (OD) of stained adherent Bio film was obtained by using a Tecan plate reader at 570 nm wavelength. Percentage inhibitions in the respective assays were calculated in comparison to the control. The results are here with tabulated in Table-7

TABLE 7

| % Inhibition | S. aureus | P. aeruginosa |
|---|---|---|
| Percentage Effect in Bio film prevention assay | | |
| Control | 0.00 | 0.00 |
| Microbicidal Composite Material | 86.21 | 83.67 |
| Ciprofloxacin 1 ug/ml | 93.10 | 89.80 |
| Percentage Effect in Bio film disruption assay | | |
| Control | 0.00 | 0.00 |
| Microbicidal Composite Material | 60.78 | 81.03 |
| Ciprofloxacin 1 ug/ml | 88.24 | 91.38 |

The results conclude that the microbicidal composite material prevents the formation of Bio films caused by *S. aureus* and *P. aeruginosa* comparable to reference standard. Further, the results also indicate that the microbicidal composite material disrupts the formed Bio film caused by *P. aeruginosa* similar to the reference standard, but mildly effectively versus Bio film formed by *S. aureus*.

Example 6

Rate of Microbicidal Effect Upon Contact with the Microbicidal Composite Material Briefly, 15 millimeter (mm) discs of the microbicidal composite material were cut and placed into 24 well plates containing approximately $10^8$ CFU/ml in Nutrient broth of *S. aureus* (ATCC 25923) & *P. aeruginosa* (ATCC 9027) respectively and incubated at 37±1° C. At intervals of 1, 5, 15, 30 and 60 minutes, broth samples were drawn and plated on nutrient agar plates and incubated for 24 hours at 37±1° C. for CFU enumeration. Two reference standards (ref-1, and ref-2) [Ref-1: Reference standard-I, includes a test material which is a cotton gauze material bonded with non siloxane based QAS and Ref-2: Reference standard-II includes a test material with active ingredient as silver Test Item refers to the 'Microbicidal Composite Material'] and a disc containing 1 μg/disc ciprofloxacin. The results are tabulated in table 8 and table 9 as percentage recovery over time. Percentage survival was calculated as number of CFU/ml in test substance/number of CFU/ml in control substance. The killing percentage was calculated as 100-residual percentage.

TABLE 8

S. aureus (ATCC 25923)

| Minutes | Control | Test Item | Ref-I | Ref-II | Ciprofloxacin |
|---|---|---|---|---|---|
| 1 | 0.00 | 0.00 | 0.00 | 0.00 | 0.00 |
| 5 | −75.79 | 40.83 | 10.92 | 31.61 | 31.98 |
| 15 | −88.36 | 88.39 | 94.31 | 61.54 | 86.2 |
| 30 | −166.07 | 93.08 | 96.49 | 73.08 | 79.11 |
| 60 | −468.85 | 98.99 | 97.57 | 97.89 | 98.76 |

TABLE 9

P. aeruginosa (ATCC 9027)

| Minutes | Control | Test item | Ref-I | Ref-II | Ciprofloxacin |
|---|---|---|---|---|---|
| 1 | 0.00 | 0.00 | 0.00 | 0.00 | 0.00 |
| 5 | −223.59 | 41.12 | 1.14 | 13.90 | 32.39 |
| 15 | −591.83 | 87.55 | 10.92 | 62.85 | 87.41 |
| 30 | −223.59 | 96.84 | 18.85 | 93.90 | 98.03 |
| 60 | −1218.26 | 99.7 | 33.93 | 98.77 | 99.88 |

Figure 4:
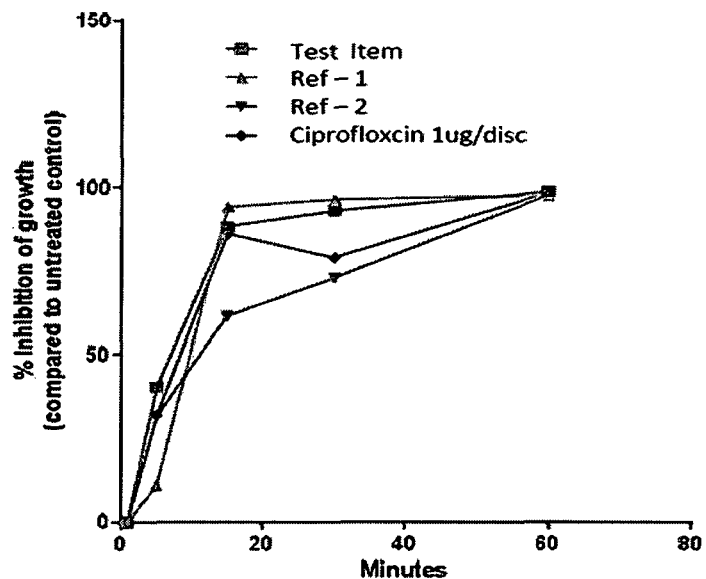
FIG. 4 illustrates a graphical representation of percentage killing of Pseudomonas aeruginosa (P. aeruginosa) with the microbicidal composite material, in comparison with reference materials and an antibiotic drug, in accordance with an embodiment of the present subject matter.
Figure 5:
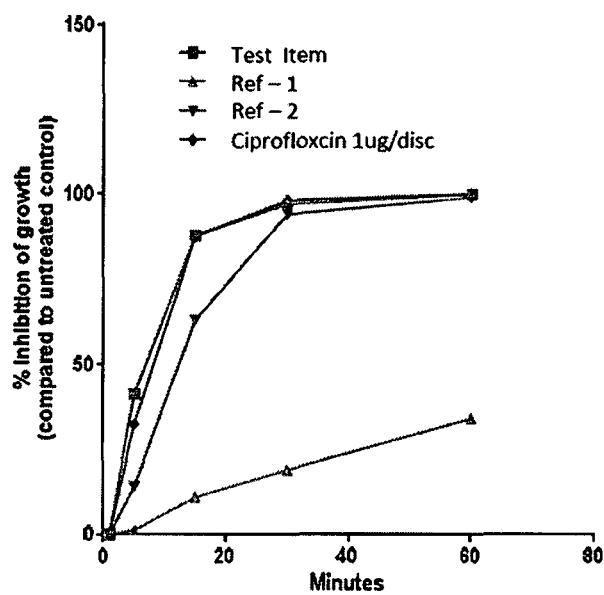
FIG. 5 illustrates a graphical representation of percentage killing of S. aureus with the microbicidal composite material, in comparison with reference materials and an antibiotic drug, in accordance with an embodiment of the present subject matter.

The test item, i.e., the microbicidal composite material exhibited a rapid inhibition of growth of both *P. aeruginosa* and *S. aureus*. The rate of kill versus *P. aeruginosa* is comparable to the reference standards (FIG. 4), while the rate of kill vs. *S. aureus* was superior to one of the reference standards (FIG. 5). FIG. 4 and FIG. 5 show the inhibition of growth as percentage in the Y-axis compared to the untreated control group. The X-axis shows time reference in this study for FIG. 4 and FIG. 5.

Example 6

In Vivo Wound Healing Assay

Sprague Dawley rats, aged 6-8 weeks were randomly distributed to various treatment groups as listed in table 10.

Each group contained 4 animals. The dorsal skins of the animals were shaved and a wound of about 2 sq·cm area was on the depilated dorsal thoracic region of animal under anaesthesia. An analgesic (ketoprofen 5 mg/kg via S.C. route) was given to minimize pain and distress. The animals are housed individually. The wound dressing material was then applied to each animal within 4 hours after the wound was created. The animals were observed daily for clinical signs and mortality. Once a week, their body weights were recorded. On days 0, 7, 14 and 28 the dressing was removed from the assigned animals and the extent of wound contraction was noted. The percentage of wound healing was calculated in comparison to the extent of the wound on day 0 within each treatment group. Since skin contain normal bacterial flora, the extent of infection in the wound was also monitored.

TABLE 10

| Group | Group ID (Barrier dressing) | Infection |
|---|---|---|
| 1 | Excision Control - no dressing | No infection |
| 2 | Reference Standard - I | No infection |
| 3 | Reference Standard - II | No infection |
| 4 | Test Item | No infection |
| 5 | Excision with *S. aureus* infection control | *Staphylococcus aureus* |
| 6 | Reference Standard - I | *Staphylococcus aureus* |
| 7 | Reference Standard - II | *Staphylococcus aureus* |
| 8 | Test Item | *Staphylococcus aureus* |
| 9 | Excision with *P. aeruginosa* infection control | *Pseudomonas aeruginosa* |
| 10 | Reference Standard - I | *Pseudomonas aeruginosa* |
| 11 | Reference Standard - II | *Pseudomonas aeruginosa* |
| 12 | Test Item | *Pseudomonas aeruginosa* |

Figure 6A:
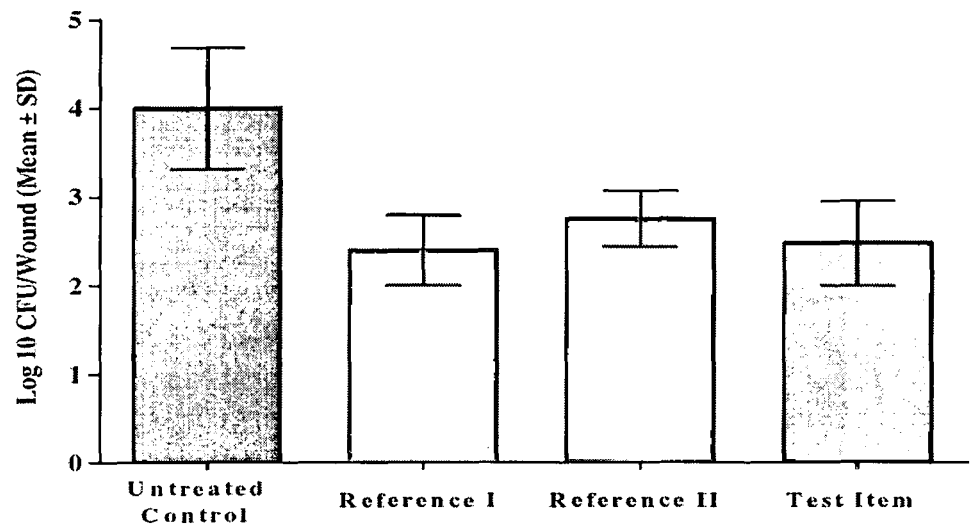
FIG. 6a illustrates a graphical representation in of bacteriological evaluation on excision wound without infection with respect to S. aureus, P. aeruginosa, after day 1 swab samples, in accordance with an embodiment of the present subject matter.
Figure 6B:
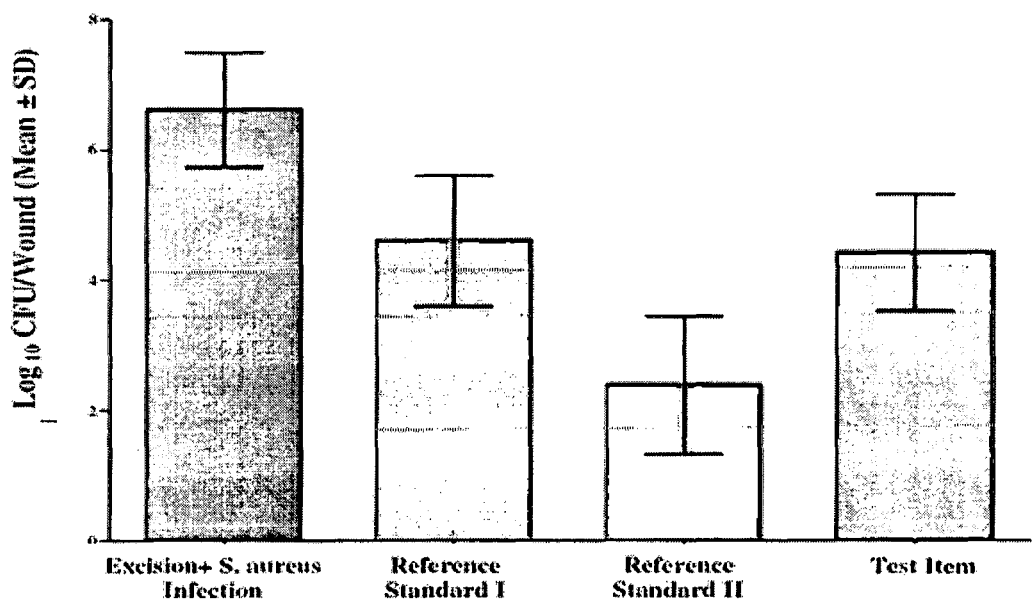
FIG. 6b illustrates a graphical representation of the killing of S. aureus with the microbicidal composite material, after day 1 swab samples, in accordance with an embodiment of the present subject matter.
Figure 6C:
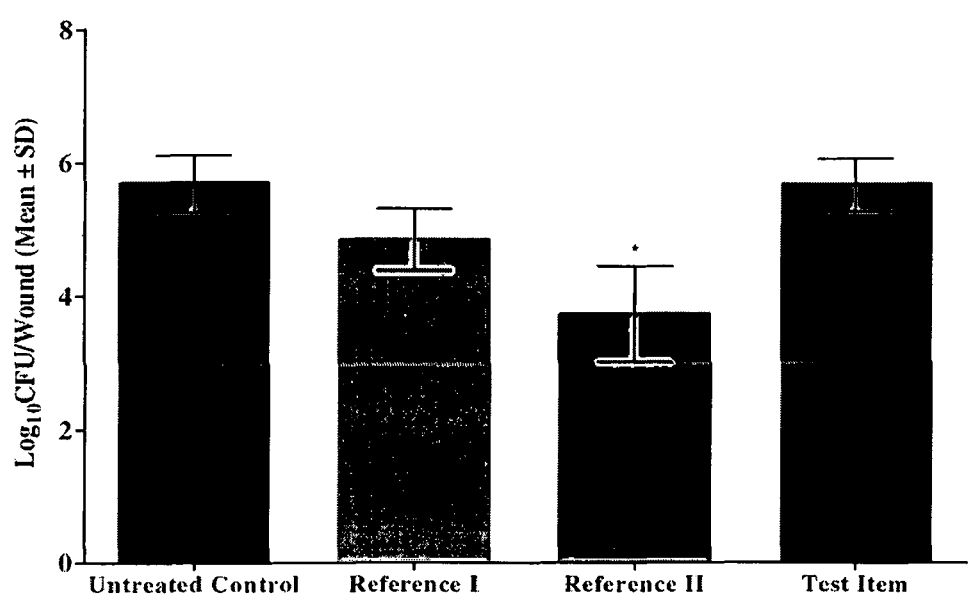
FIG. 6c illustrates a graphical representation of the killing of P. aeruginosa with the microbicidal composite material, after day 1 swab samples, in accordance with an embodiment of the present subject matter.
Figure 7A:
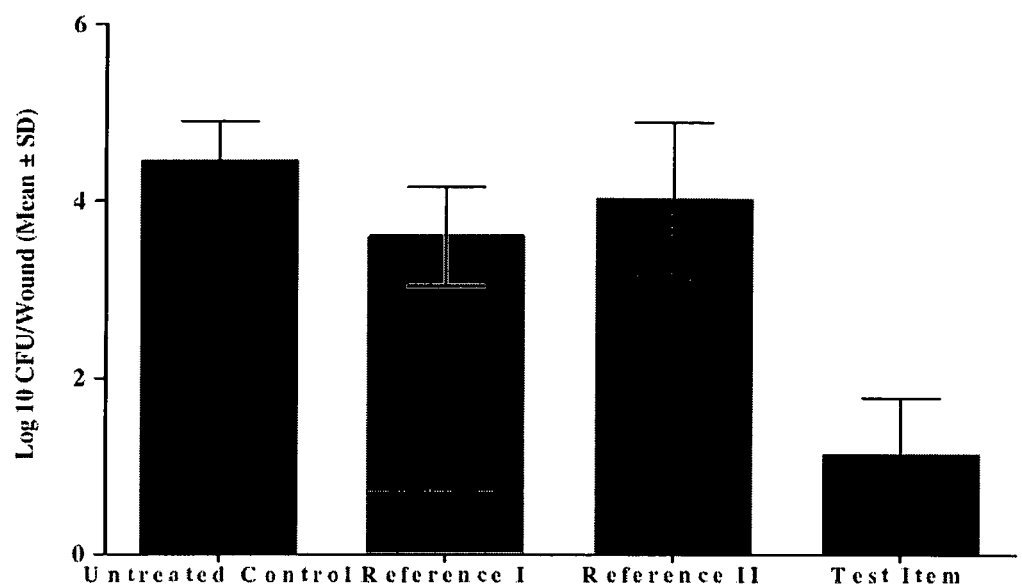
FIG. 7a illustrates a graphical representation of bacteriological evaluation on excision wound without infection with respect to S. aureus, P. aeruginosa, after day 7 swab samples, in accordance with an embodiment of the present subject matter.
Figure 7B:
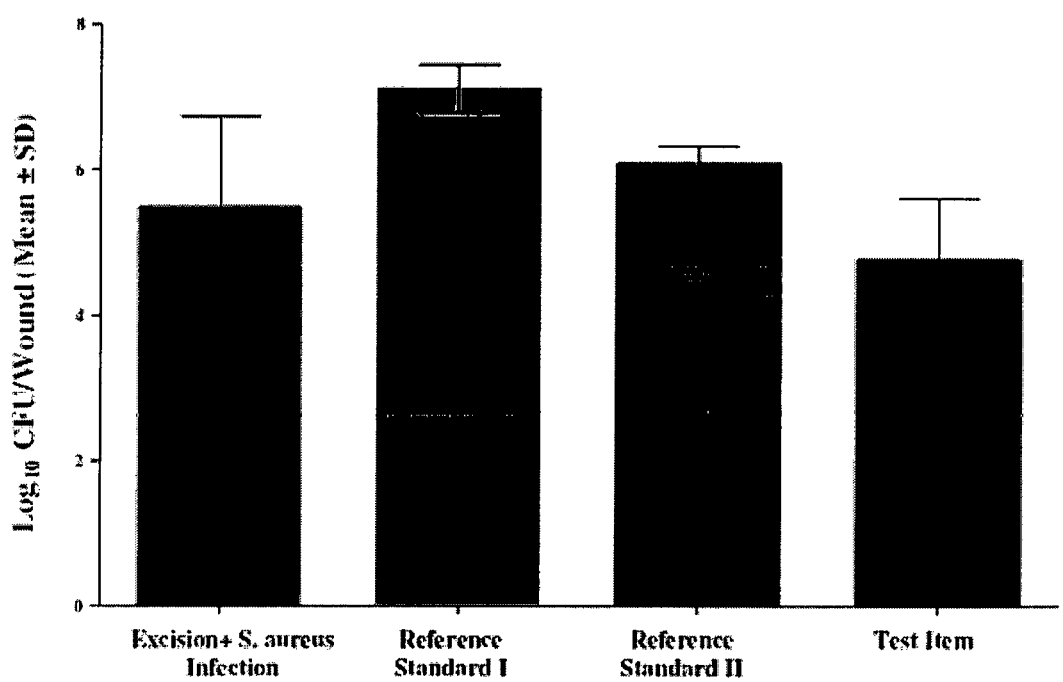
FIG. 7b illustrates a graphical representation of the killing of S. aureus with the microbicidal composite material, after day 7 swab samples, in accordance with an embodiment of the present subject matter.
Figure 7C:
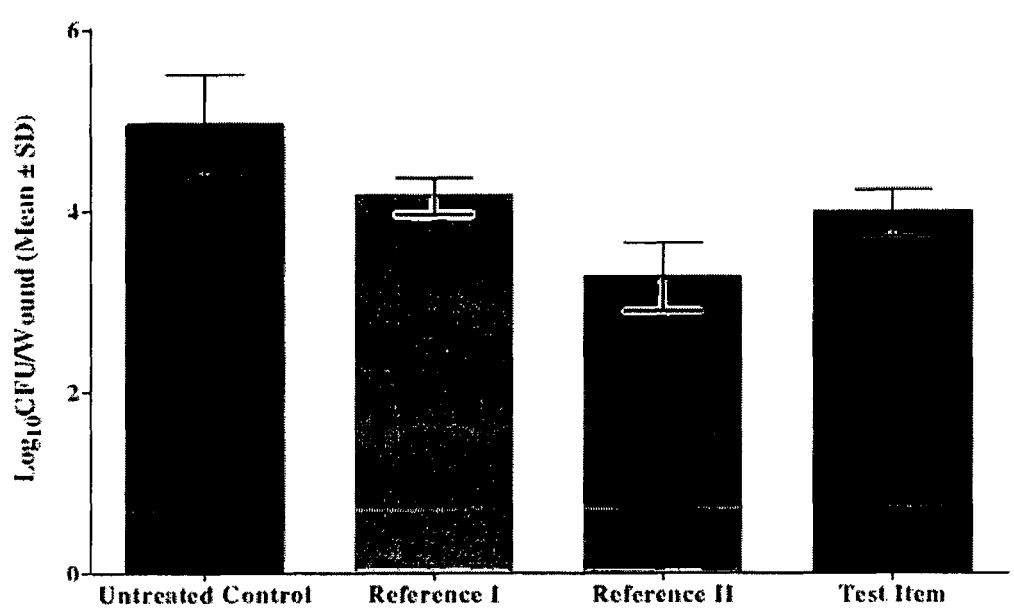
FIG. 7c illustrates a graphical representation of the killing of P. aeruginosa with the microbicidal composite material, after day 7 swab samples, in accordance with an embodiment of the present subject matter.
Figure 8A:
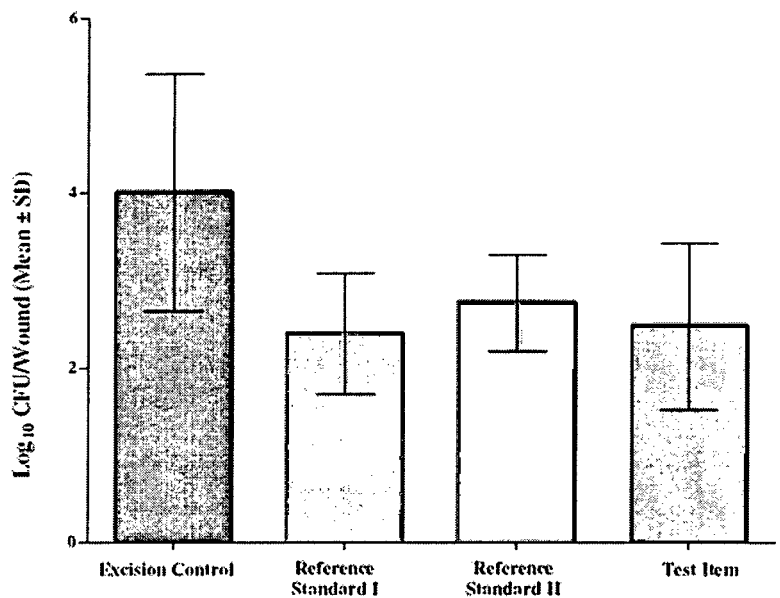
FIG. 8a illustrates a graphical representation of bacteriological evaluation on excision wound without infection with respect to S. aureus, P. aeruginosa, after day 28 swab samples, in accordance with an embodiment of the present subject matter.
Figure 8B:
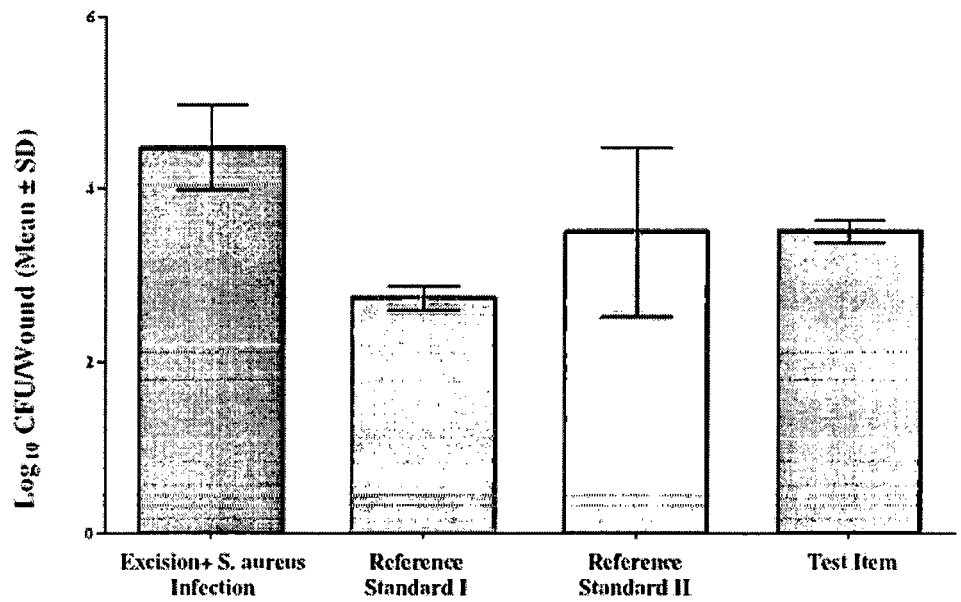
FIG. 8b illustrates a graphical representation of the killing of S. aureus with the microbicidal composite material, after day 28 swab samples, in accordance with an embodiment of the present subject matter.
Figure 8C:
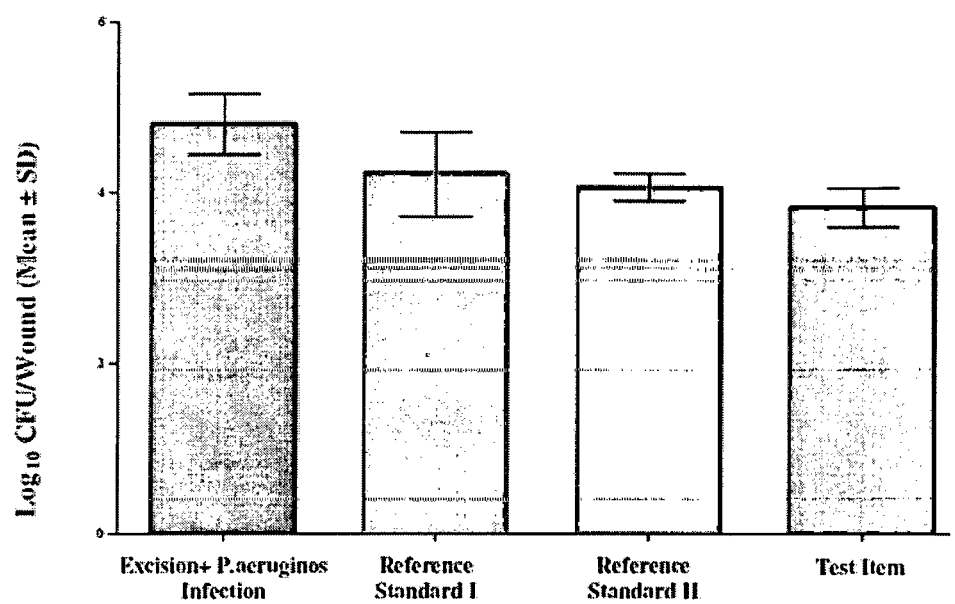
FIG. 8c illustrates a graphical representation of the killing of P. aeruginosa with the microbicidal composite material, after day 28 swab samples, in accordance with an embodiment of the present subject matter.

Studies were conducted when the excision wound was not subjected to external introduction of infection, when the excision wound was subjected to external introduction of *S. aureus* infection, and when the excision wound was subjected to external introduction of *P. aeruginosa* infection. Under all the above 3 conditions mentioned, it was observed that the test item, i.e., the microbicidal composite material heals the wound around twice as fast as the nearest reference standard in terms of wound contraction. Also, the test item reduces the infection load at the site of the wound multi fold better than the nearest reference standard by day 7, 14, and day 28. The figures FIGS. 6a, 6b, and 6c show the representation of the microbicidal action of the microbicidal composite material with the killing representation represented by the quantitative units of Colony Forming Units (CFU). This unit of measurement, as known in the art is in logarithmic representation estimating the microbicidal effect. FIG. 6a, illustrates for the estimation on day 1 evaluation on excision wound without infection with respect to *S. aureus, P. aeruginosa*, using day 1 swab samples. FIG. 6b, illustrates for the estimation on day 1 evaluation on excision wound with infection with respect to *S. aureus*, using day 1 swab samples. FIG. 6c, illustrates for the estimation on day 1 evaluation on excision wound with infection with respect to *P. aeruginosa*, using day 1 swab samples. Similarly FIG. 7a, FIG. 7b and FIG. 7c illustrates the quantitative microbicidal action on day 7, and FIG. 8a, FIG. 8b and FIG. 8c illustrates the quantitative microbicidal action on day 28.

Figure 9A:
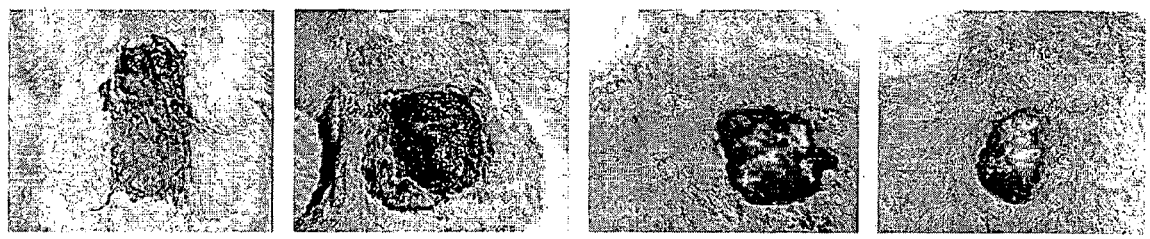
FIG. 9a illustrates a pictorial illustration of bacteriological evaluation on excision wound healing in rats, in terms of wound contraction without infection with respect to S. aureus, P. aeruginosa after day 7, in accordance with an embodiment of the present subject matter.
Figure 9B:
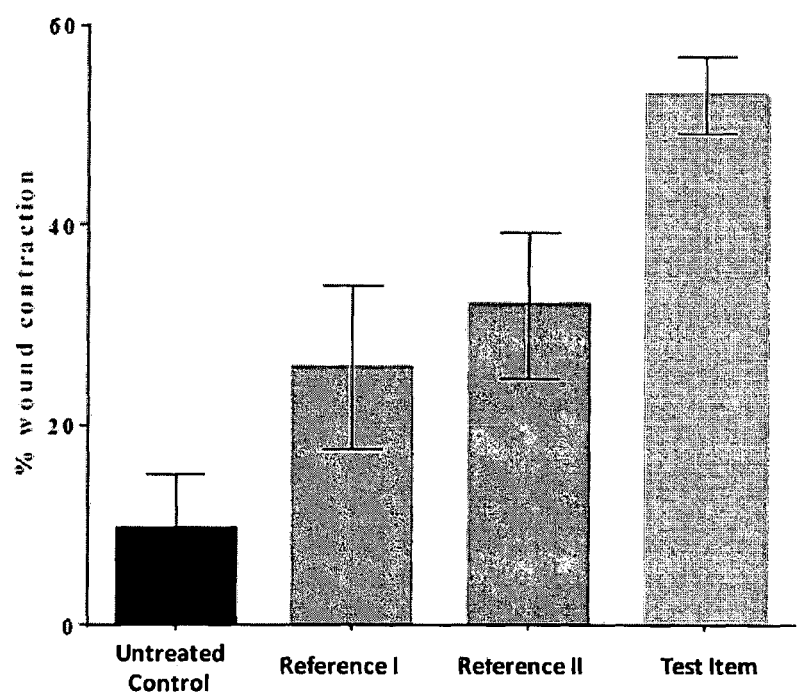
FIG. 9b illustrates a graphical representation of percentage contraction of the excision wound in quantitative terms without infection with respect to S. aureus, P. aeruginosa after day 7, in accordance with an embodiment of the present subject matter.
Figure 10A:
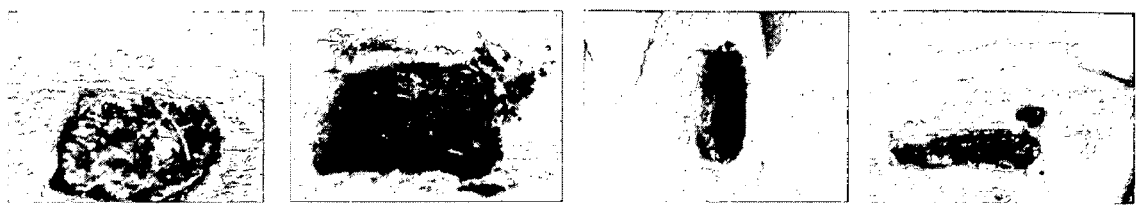
FIG. 10a illustrates a pictorial illustration of bacteriological evaluation on excision wound healing in rats, in terms of wound contraction with respect to S. aureus, after day 7, in accordance with an embodiment of the present subject matter.
Figure 10B:
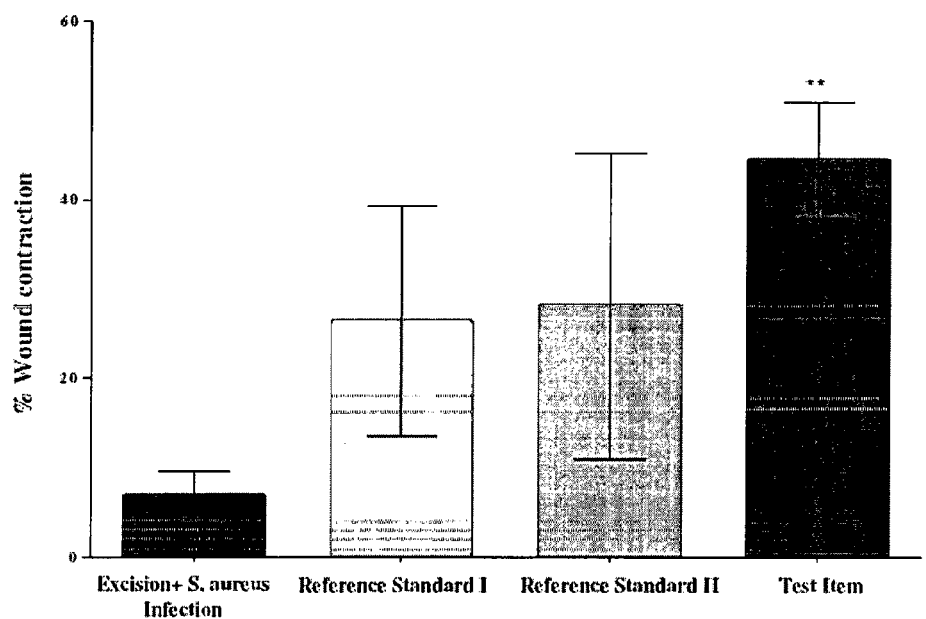
FIG. 10b illustrates a graphical representation of percentage contraction of the excision wound in quantitative terms with infection with respect to S. aureus, after day 7, in accordance with an embodiment of the present subject matter.
Figure 11A:
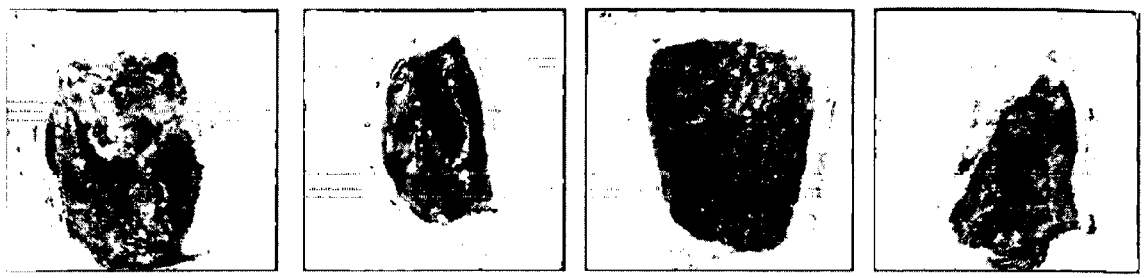
FIG. 11a illustrates a pictorial illustration of bacteriological evaluation on excision wound healing in rats, in terms of wound contraction with respect to P. aeruginosa, after day 7, in accordance with an embodiment of the present subject matter.
Figure 11B:
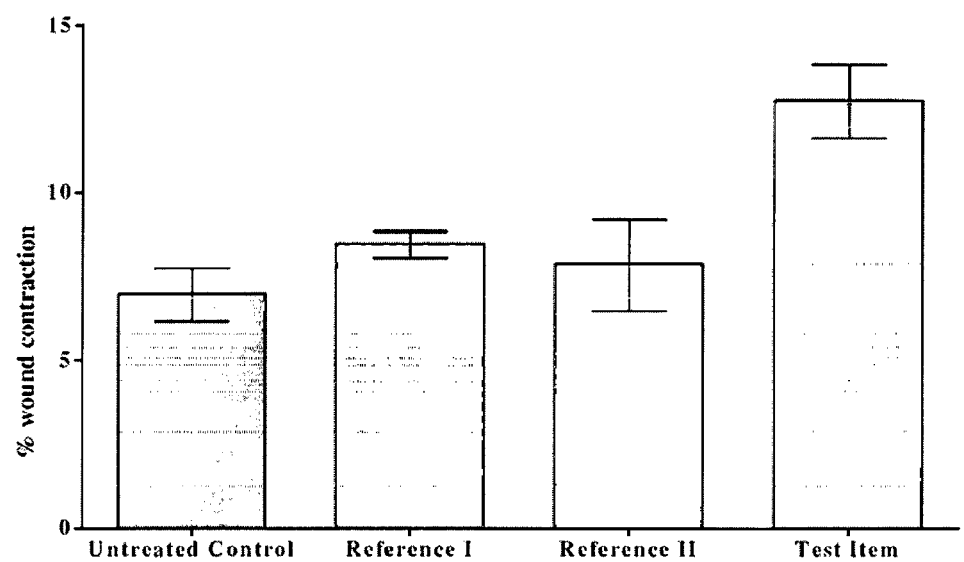
FIG. 11b illustrates a graphical representation of percentage contraction of the excision wound in quantitative terms with infection with respect to *P. aeruginosa*, after day 7, in accordance with an embodiment of the present subject matter.
Figure 12A:
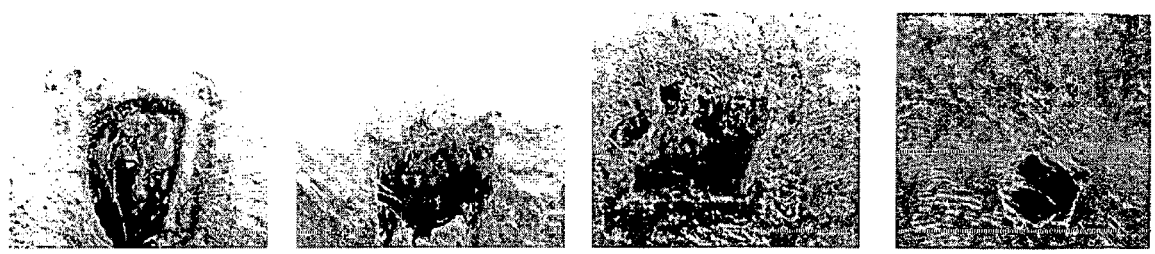
FIG. 12a illustrates a pictorial illustration of bacteriological evaluation on excision wound healing in rats, in terms of wound contraction without infection with respect to *S. aureus, P. aeruginosa* after day 14, in accordance with an embodiment of the present subject matter.
Figure 12B:
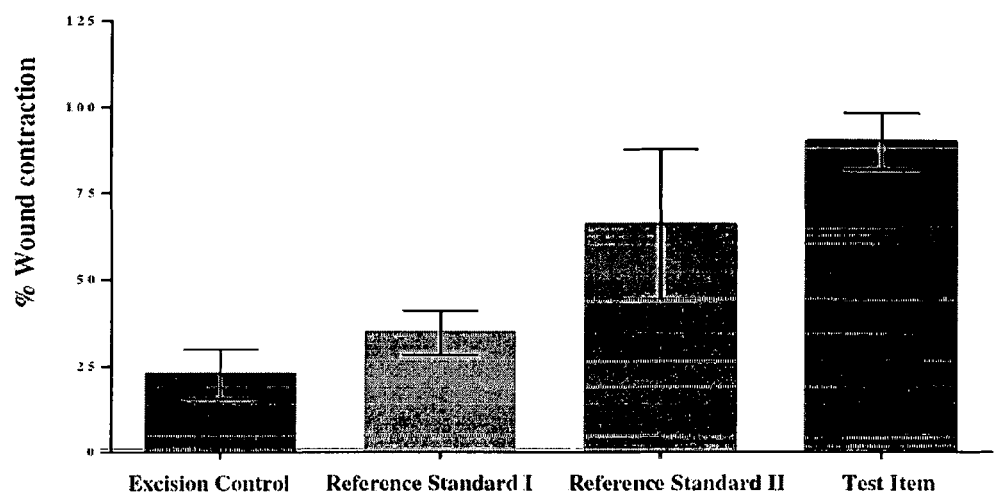
FIG. 12b illustrates a graphical representation of percentage contraction of the excision wound in quantitative terms without infection with respect to *S. aureus, P. aeruginosa* after day 14, in accordance with an embodiment of the present subject matter.
Figure 13A:
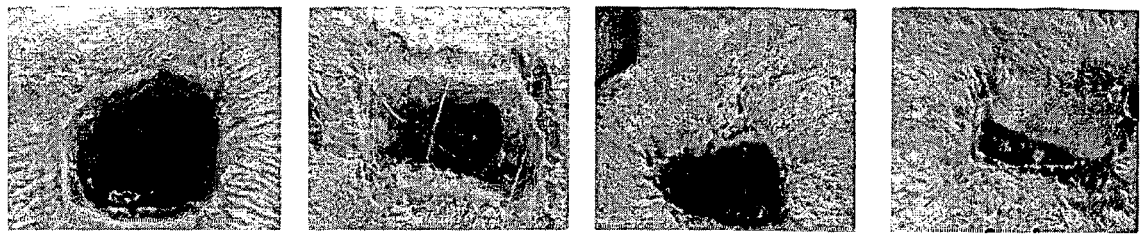
FIG. 13a illustrates a pictorial illustration of bacteriological evaluation on excision wound healing in rats, in terms of wound contraction with respect to *S. aureus*, after day 14, in accordance with an embodiment of the present subject matter.
Figure 13B:
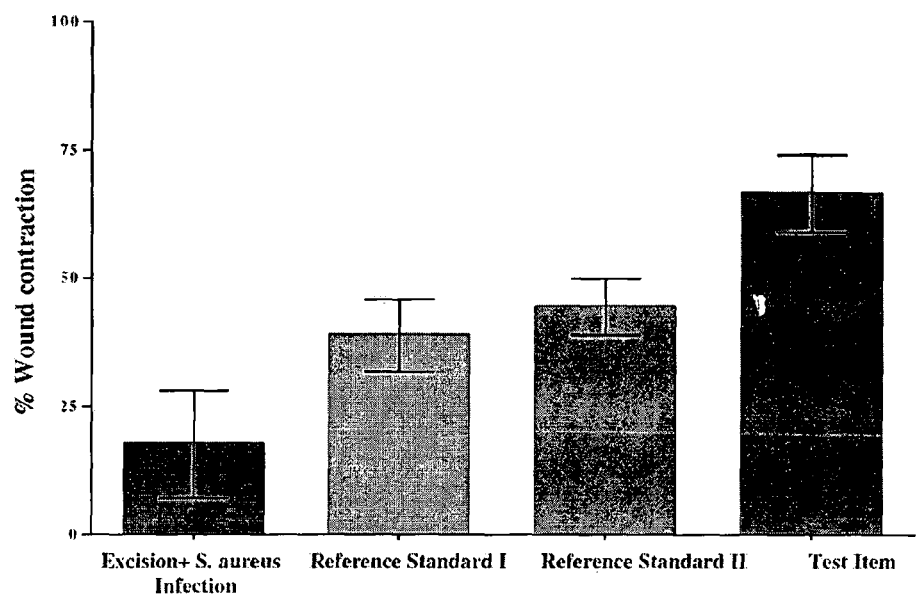
FIG. 13b illustrates a graphical representation of percentage contraction of the excision wound in quantitative terms with infection with respect to *S. aureus*, after day 14, in accordance with an embodiment of the present subject matter.
Figure 14A:
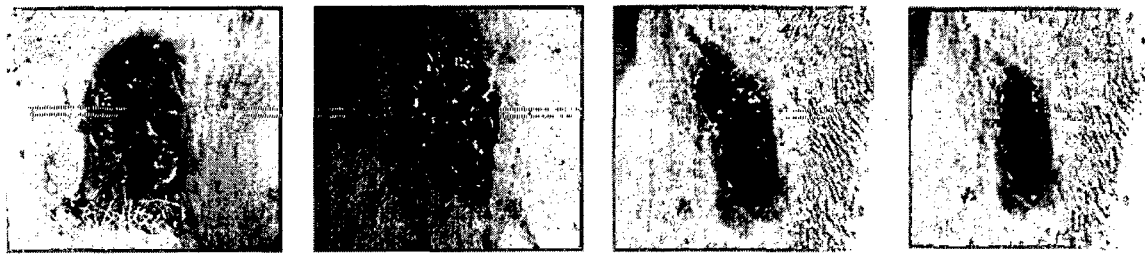
FIG. 14a illustrates a pictorial illustration of bacteriological evaluation on excision wound healing in rats, in terms of wound contraction with respect to *P. aeruginosa*, after day 14, in accordance with an embodiment of the present subject matter.
Figure 14B:
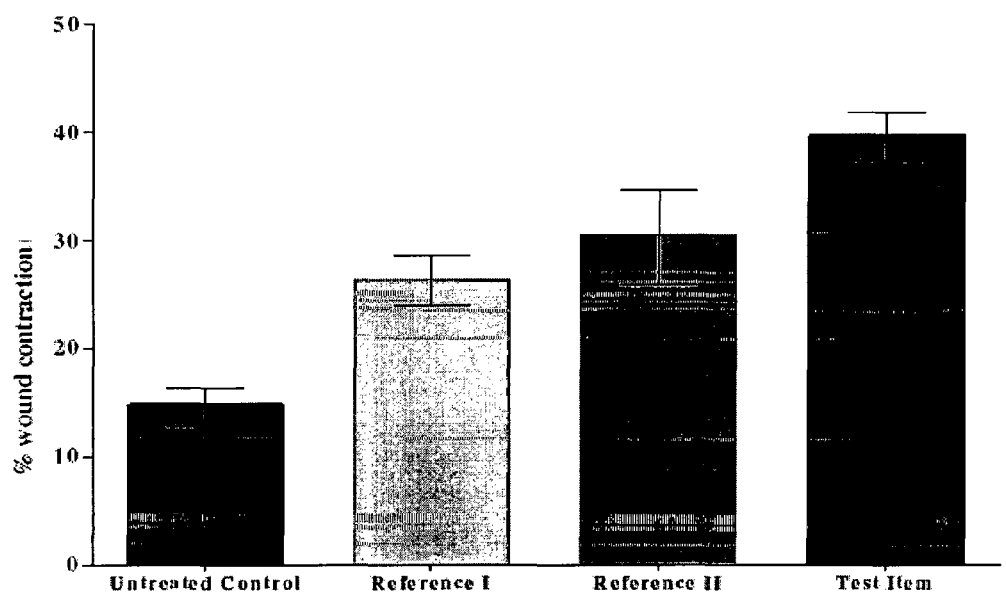
FIG. 14b illustrates a graphical representation of percentage contraction of the excision wound in quantitative terms with infection with respect to *P. aeruginosa*, after day 14, in accordance with an embodiment of the present subject matter.
Figure 15A:
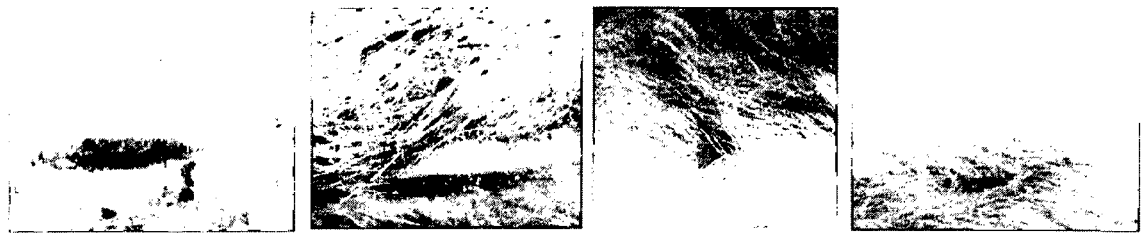
FIG. 15a illustrates a pictorial illustration of bacteriological evaluation on excision wound healing in rats, in terms of wound contraction without infection with respect to *S. aureus, P. aeruginosa* after day 28, in accordance with an embodiment of the present subject matter.
Figure 15B:
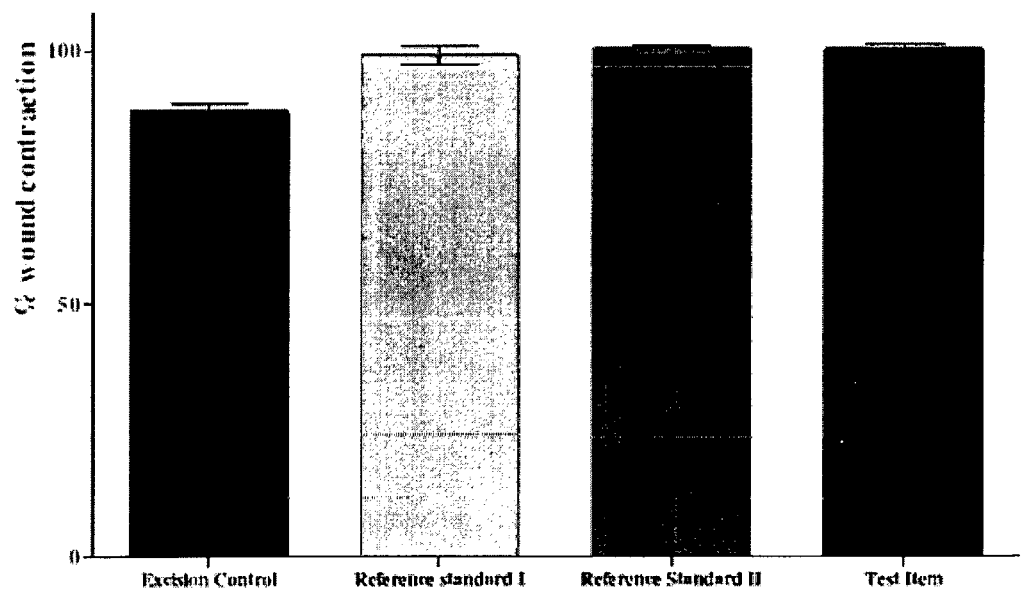
FIG. 15b illustrates a graphical representation of percentage contraction of the excision wound in quantitative terms without infection with respect to *S. aureus, P. aeruginosa* after day 28, in accordance with an embodiment of the present subject matter.
Figure 16A:
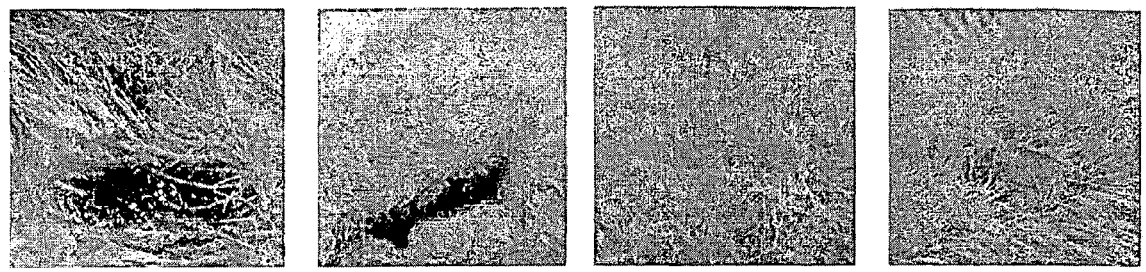
FIG. 16a illustrates a pictorial illustration of bacteriological evaluation on excision wound healing in rats, in terms of wound contraction with respect to *S. aureus*, after day 28, in accordance with an embodiment of the present subject matter.
Figure 16B:
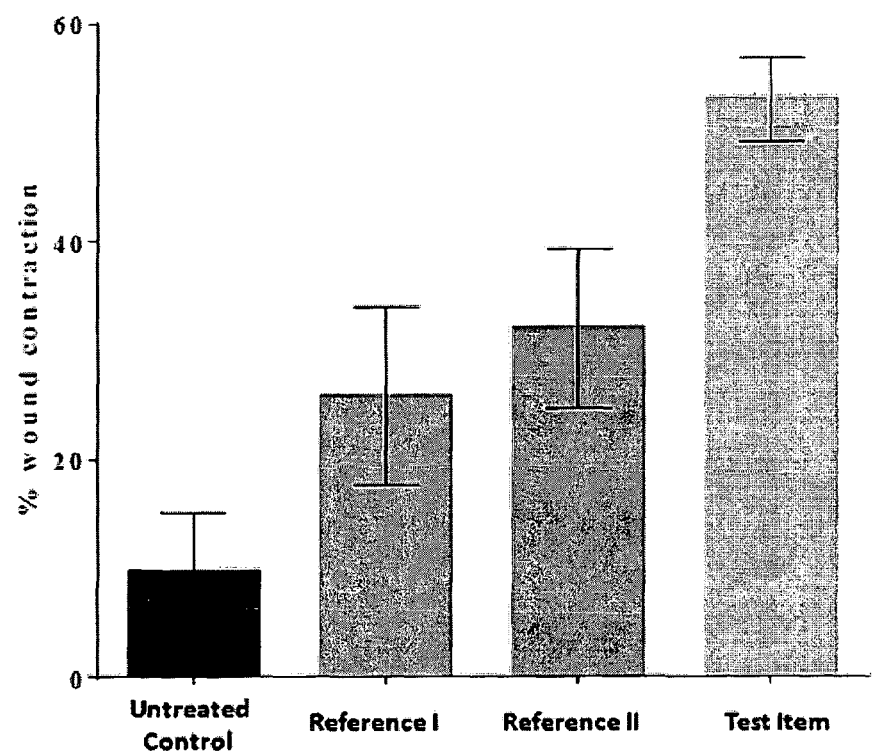
FIG. 16b illustrates a graphical representation of percentage contraction of the excision wound in quantitative terms with infection with respect to *S. aureus*, after day 28, in accordance with an embodiment of the present subject matter.
Figure 17A:
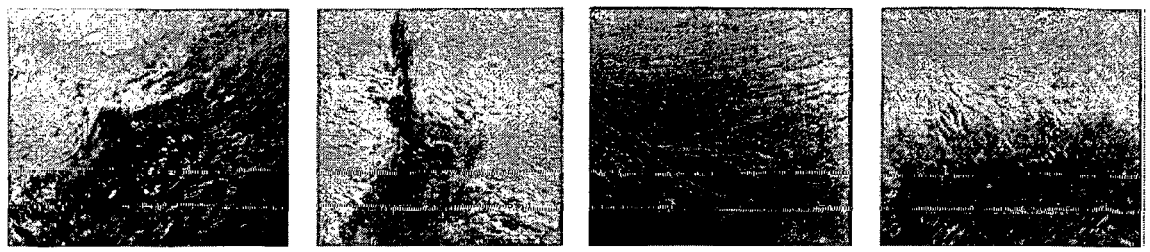
FIG. 17a illustrates a pictorial illustration of bacteriological evaluation on excision wound healing in rats, in terms of wound contraction with respect to *P. aeruginosa*, after day 28, in accordance with an embodiment of the present subject matter.
Figure 17B:
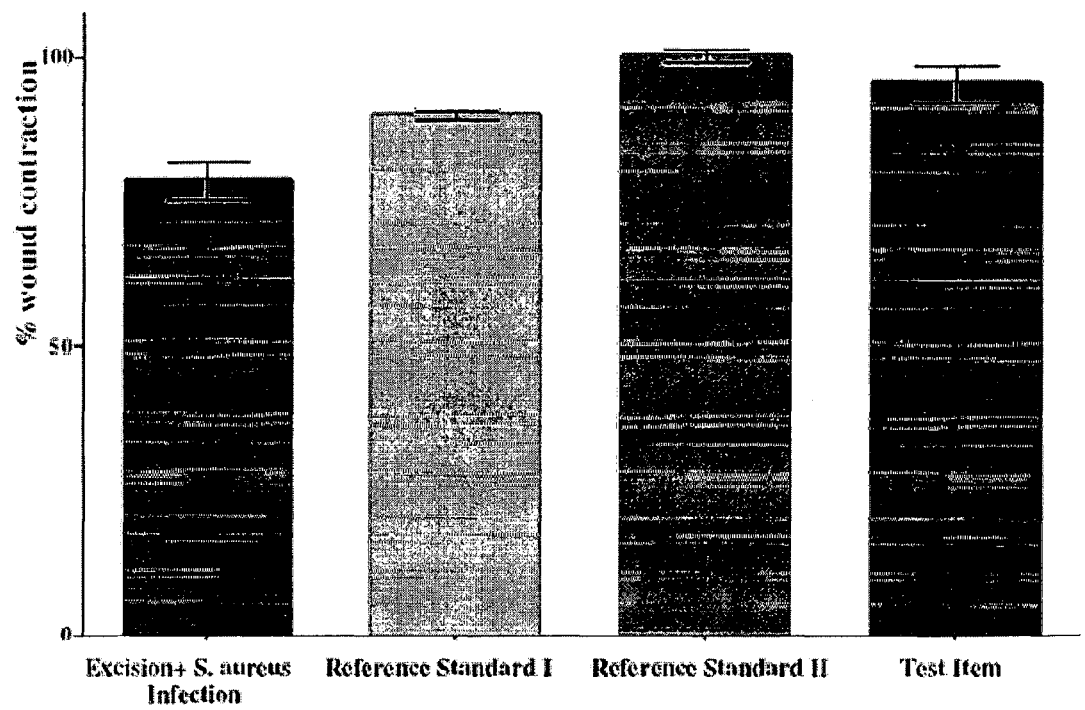
FIG. 17b illustrates a graphical representation of percentage contraction of the excision wound in quantitative terms with infection with respect to *P. aeruginosa*, after day 28, in accordance with an embodiment of the present subject matter.

FIG. 9a is a pictorial representation of the excision wound and its contraction that is dressed with this microbicidal composite material without any infection of the microbes with a control and two reference standards of wound dressing and the wound dressing in this subject matter on day 7. FIG. 9b gives the quantitative estimate with of the wound contraction for infection without any infection of the microbes after day 7 with the control, two reference standards and the wound dressing in this subject matter. FIG. 10a and FIG. 10b illustrate similarly for infection with *S. aureus* after day 7. FIG. 11a and FIG. 11b illustrate similarly for infection with *P. aeruginosa* after day 7. In a similar way FIG. 12a, FIG. 12b, FIG. 13a, FIG. 13b, FIG. 14a and FIG. 14b illustrate the effect after day 14. In yet another similar way FIG. 15a, FIG. 15b, FIG. 16a, FIG. 16b, FIG. 17a and FIG. 17b illustrate the effect after day 28.

Example 7

Test for In Vitro Cytotoxicity: Direct Contact Method

Based on the results obtained in the study, it is concluded that the test item Microbicidal composite material is considered non cytotoxic under the condition of the present test carried out using BALB/c 3T3 cells line.

Example 8

Test for Skin Sensitization

The extracts of the test item Microbicidal Wound dressing did not show any sensitization reaction. Hence it is concluded that the test item microbicidal composite material 100 is Non Sensitized under the condition of the present study.

Example 9

Test for Intracutaneous Reactivity Study in New Zealand Rabbits

The extract of the test item Microbicidal wound dressing did not show any intracutaneous reactivity. Hence it is concluded that the test item, microbicidal composite material, meets the requirements of ISO 10993, Part-10:2010(E) under the conditions of the present study.

Example 10

Test for Acute Systematic Toxicity Study in Swiss Albino Mice

The Extracts of the test item Microbicidal composite material did not show any systematic toxicity. Hence it is concluded that the test item Microbicidal Wound dressing, meets the requirements of ISO 10993, Part-11: 2006 (E) under the conditions of the present study.

CONCLUSION

In light of the foregoing description, a person skilled in the art will appreciate the advantages of the embodiments, some of which are mentioned below.
1) The microbicidal composite material 100 may be used in several products, such as air sanitary pad, tampons, toilet accessories, diaper, sanitary wipe, surgical gown, surgical glove, surgical scrub, mattress covers, beddings, bedding sheets and pillow covers, operation theatre covers, hospital examination table covers, hospital bio waste disposable bags, hospital curtains, and air conditioning filters, water filters, face mask, meat storage and packing materials and other products as may be understood by a person skilled in the art, to exhibit microbicidal properties.

2) The microbicidal composite material 100 of the embodiments, when used either as a whole or part in wound dressing, avoids contamination of wound by external pathogens.

3) The microbicidal composite material 100 of the embodiments, when used either as a whole or part in wound dressing kills pathogens present in the exudates, thereby preventing infection for relatively longer period of time.

4) The microbicidal composite material 100 of the embodiments, when used either as a whole or part in wound dressing, facilitates wicking away of the exudates from the wound, due to the increased differential stitch/thread density in the three dimensional structure, and dries the same by simple evaporation method.

5) The microbicidal composite material 100 of the embodiments, when used either as a whole or part in wound dressing enables air circulation around the wound, thereby facilitating faster healing of the wound by oxygenation of the tissues.

6) The microbicidal composite material 100 of the embodiments, when used either as a whole or part in wound dressing, as a result of having non-eluting property, provides a substantial active concentration over the entire time period of use as a wound dressing. Also it is ensuring that evolutionary drug resistance is not built up by the pathogen which happens when the active concentration of the bactericidal component goes below a threshold value due to eluting of microbicidal ingredient and the pathogen transform to develop its own protection mechanism rendering the drug ineffective.

7) The microbicidal composite material 100 of the embodiments, when used either as a whole or part in wound dressing passes the USP 51 barrier study for not allowing growth of pathogens till 28 days. In other words, the wound can be theoretically left unattended, with the microbicidal composite material 100 being used for dressing, for 28 days, depending on the wound type without any risk of infections.

It shall be noted that some of the processes described above are described as sequence of steps; this was done solely for the sake of illustration. Accordingly, it is contemplated that some steps may be added, some steps may be omitted, the order of the steps may be re-arranged, or some steps may be performed simultaneously.

Although embodiments have been described with reference to specific example embodiments, it will be evident that various modifications and changes may be made to these embodiments without departing from the broader spirit and scope of the system and method described herein. Accordingly; the specification and drawings are to be regarded in an illustrative rather than a restrictive sense.

Many alterations and modifications of the present subject matter will no doubt become apparent to a person of ordinary skill in the art after having read the foregoing description. It is to be understood that the phraseology or terminology employed herein is for the purpose of description and not of limitation. It is to be understood that the description above contains many specifications; these should not be construed as limiting the scope of the present subject matter but as merely providing illustrations of some of the personally preferred embodiments of this present subject matter.

Thus the scope of the present subject matter should be determined by the appended claims and their legal equivalents rather than by the examples given.

We claim:

1. A microbicidal composite material comprising:
   a first layer having a first pre-defined thickness and a first predefined stitch/thread density;
   a second layer having a second pre-defined thickness and a second predefined stitch/thread density; and
   an intermediate layer having a third pre-defined thickness and a third predefined stitch/thread density wherein the intermediate layer is sandwiched between and connected to the first layer and the second layer to form a three dimensional structure by one of knitting and weaving, wherein each layer in the three dimensional structure has plurality of apertures to allow for circulation of air through the microbicidal composite material;
   wherein each of the plurality of apertures is associated with a pre-determined size and wherein the pre-determined size of the apertures is controlled by course per inch and wales per inch of the one of knitting and weaving process;
   wherein the third pre-defined stitch/thread density is less than the first pre-defined stitch/thread density and the second pre-defined stitch/thread density, to allow for wicking of a fluid on contact of at least one of the first layer and the second layer with the fluid; and
   wherein each layer of the three-dimensional structure comprises surface moieties cross linked to a microbicidal agent in a non-eluting manner.

2. The microbicidal composite material of claim 1, wherein the first pre-defined thickness is in the range of 100 micron to 1000 micron.

3. The microbicidal composite material of claim 1, wherein the second pre-defined thickness is in the range of 100 micron to 1000 micron.

4. The microbicidal composite material of claim 1, wherein the third pre-defined thickness is in the range of 600 micron to 6000 micron.

5. The microbicidal composite material of claim 1, wherein the fluid is a bio fluid.

6. The microbicidal composite material of claim 1, wherein each layer in the three dimensional structure is permeable to fluids and gases.

7. The microbicidal composite material of claim 1, wherein each layer in the three dimensional structure comprises at least one material selected from a group consisting of natural fibers, synthetic fibers, and regenerated fibers selected from the group consisting of polyester, acrylic, polyamide, polyurethane, regenerated cellulose, poly acylonitriles, polytriphenylene terephthalate, polybutylene terephthalate, polylactic acid, aramides, metaramides, nylon6, nylon 6.6, polypropylene, polyethylene, poly-p-phenyleneteraphthalamid, poly-m-phenyleneteraphthalamide, natural rubber, wool, cotton, flax, rayon, jute, and linen.

8. The microbicidal composite material of claim 7, wherein at least one layer in the three dimensional structure is composed of an elastomeric material selected from the group consisting of textured yarns/fibers, multi component yarns/fibers, polyurethane and natural rubber to impart resilient property.

9. The microbicidal composite material of claim 1, wherein the microbicidal agent cross linked to surface moieties is a compound of Formula I

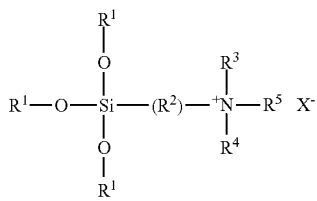

Formula I wherein:
R¹ is independently selected from hydrogen or $C_1$ to $C_4$ alkyl;
R² is a divalent hydrocarbon radical with $C_1$ to $C_8$ carbon atoms;
R³ is independently selected from hydrogen or $C_1$ to $C_4$ alkyl;
R⁴ is independently selected from hydrogen or $C_1$ to $C_{10}$ alkyl;
R⁵ is a $C_8$ to $C_{22}$ saturated or unsaturated hydrocarbon radical; and
X is counter anion selected from the group consisting of $Cl^-$, $Br^-$, $I^-$, $OH^-$, $HCO_3^-$, $CO_3^{2-}$.

10. The microbicidal composite material of claim 9, wherein the microbicidal agent is one selected from the group consisting of 3-(trimethoxysilyl)propyl-N-octadecyl-N,N-dimethyl ammonium chloride, 3-(trimethoxysilyl)propyl-N-tetradecyl-N,N-dimethyl ammonium chloride, 3-(trimethoxysilyl) propyl-N,N-didecyl-N-methyl ammonium chloride, and 3-(trihydroxysilyl) propyl-N-octadecyl-N,N-dimethyl ammonium chloride.

11. The microbicidal composite material of claim 1, wherein the microbial composite material is used in whole or part of wound dressing.

12. The microbicidal composite material of claim 1, wherein the microbial composite material is used to treat a wound caused by one or more of a gram positive bacteria, gram negative bacteria, virus and fungi, or a combination thereof.

13. The microbicidal composite material of claim 1, wherein the microbial composite material is used as a filter for sterilizing at least one of fluid of air, water, and milk, or a combination thereof.

14. The microbicidal composite material of claim 1, wherein the microbial composite material is for use in whole or part of, one or more of a sanitary pad, tampons, toilet accessories, diaper, sanitary wipe, surgical gown, surgical glove, surgical scrub, mattress covers, beddings, bedding sheets and pillow covers, operation theatre covers, hospital examination table covers, hospital bio waste disposable bags, hospital curtains, air conditioning filters, face mask, meat storage, and packing materials.

15. The microbicidal composite material of claim 1, wherein each layer in the three dimensional structure comprises at least one of a microfiber and a nanofiber for augmentation of available surface moieties, wherein the augmented surface moieties allow for a greater concentration of the bound microbicidal agent as compared to a surface without the surface augmentation.

16. The microbicidal composite material of claim 1, wherein the knitting is spacer knitting and the weaving is spacer weaving.

17. A wound dressing comprising the microbicidal composite material of claim 1, in part or in whole.

18. The wound dressing of claim 17, wherein the first pre-defined thickness is in the range of 100 micron to 1000 micron.

19. The wound dressing of claim 17, wherein the second pre-defined thickness is in the range of 100 micron to 1000 micron.

20. The wound dressing of claim 17, wherein the third pre-defined thickness is in the range of 600 micron to 6000 micron.

21. The wound dressing of claim 17, wherein each layer in the three dimensional structure is selectively permeable to body fluids and gases from the wound.

22. The wound dressing of claim 17,
wherein each layer in the three dimensional structure is composed of at least one material selected from the group consisting of natural fibers, synthetic fibers, regenerated fibers, and a combination thereof,
wherein the regenerated fibers are selected from the group consisting of polyester, acrylic, polyamide, polyurethane, regenerated cellulose, poly acylonitriles, textured polyethylene terephthalate, polytriphenylene terephthalate, polybutylene terephthalate, polylactic acid, aramides, metaramides, nylon6, nylon 6.6, polypropylene, polyethylene, poly-p-phenyleneteraphthalamid, poly-m-phenyleneteraphthalamide, natural rubber, wool, cotton, flax, rayon, jute and linen, and a combination thereof.

23. The wound dressing of claim 17, wherein at least one layer in the three dimensional structure is composed of a biopolymer, and wherein the biopolymer includes at least one material selected from the group consisting of poly lactic acid, poly glycolic acid, and caprolactum.

24. The wound dressing of claim 23, wherein at least one layer in the three dimensional structure comprises bioactive agents to impart sustained and time release of the bioactive agents, and wherein the bioactive agents include at least one bioactive agent selected from the group consisting of vitamins, minerals, anti inflammatory agents, antibiotics, antiseptic, haemostatic agents and analgesics.

25. The wound dressing of claim 17, wherein at least one layer in the three dimensional structure comprises an elastomeric material, and wherein the elastomeric material is selected from the group consisting of a textured yarns/fibers, multi component yarns/fibers, polyurethane and natural rubber to impart resilient property.

26. The wound dressing of claim 17, wherein the microbicidal agent cross linked to the augmented surface moieties is a compound of Formula I

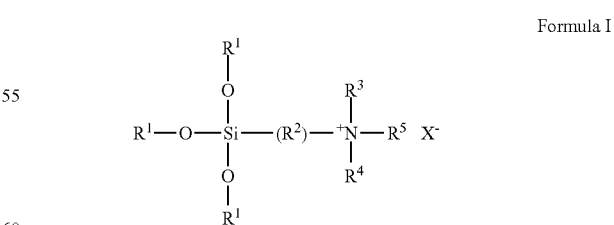

Formula I wherein:
R¹=hydrogen and/or $C_1$ to $C_4$ alkyl;
R²=divalent hydrocarbon radical with $C_1$ to $C_8$ carbon atoms;
R³=hydrogen or $C_1$ to $C_4$ alkyl;
R⁴=hydrogen or $C_1$ to $C_{10}$ alkyl;

$R^5 = C_8$ to $C_{22}$ saturated or unsaturated hydrocarbon radical; and

X=alkyl halide.

27. The wound dressing material of claim 26, wherein the microbicidal agent is one selected from the group consisting of 3-(trimethoxysilyl)propyl-N-octadecyl-N, N-dimethyl ammonium chloride, 3-(trimethoxysilyl)propyl-N-tetradecyl-N,N-dimethyl ammonium chloride, 3-(trimethoxysilyl)propyl-N,N-didecyl-N-methyl ammonium chloride, and 3-(trihydroxysilyl) propyl-N-octadecyl-N,N-dimethyl ammonium chloride.

28. The wound dressing of claim 17, wherein each layer in the three dimensional structure comprises at least one of a microfiber and a nanofiber for augmentation of available surface moieties, wherein the augmented surface moieties allow for a greater concentration of the bound microbicidal agent.

29. The wound dressing of claim 17, wherein the knitting is spacer knitting and the weaving is spacer weaving.

* * * * *